US012569325B2

(12) United States Patent
Berg et al.

(10) Patent No.: US 12,569,325 B2
(45) Date of Patent: Mar. 10, 2026

(54) DEVICE FOR USE WITH BODY TISSUE SPHINCTERS

(71) Applicant: JT GODFREY, LLC, Hugo, MN (US)

(72) Inventors: James Godfrey Berg, Centerville, MN (US); Thomas Godfrey Berg, Centerville, MN (US)

(73) Assignee: JT GODFREY, LLC, Hugo, MN (US)

( * ) Notice: Subject to any disclaimer, the term of this patent is extended or adjusted under 35 U.S.C. 154(b) by 291 days.

(21) Appl. No.: 18/123,896

(22) Filed: Mar. 20, 2023

(65) Prior Publication Data

US 2023/0225845 A1     Jul. 20, 2023

Related U.S. Application Data

(63) Continuation of application No. 15/931,221, filed on May 13, 2020, now Pat. No. 11,628,052.

(51) Int. Cl.
*A61F 2/00* (2006.01)
*A61P 17/02* (2006.01)

(52) U.S. Cl.
CPC ........... *A61F 2/0036* (2013.01); *A61P 17/02* (2018.01); *A61F 2210/0004* (2013.01); *A61F 2210/0057* (2013.01)

(58) Field of Classification Search
CPC ............ A61F 2/0036; A61F 2210/0004; A61F 2210/0057; A61F 2002/91508; A61F 2002/91516; A61F 2210/0014; A61F 5/005; A61F 2230/0065; A61B 2017/00827; A61B 2017/00893
See application file for complete search history.

(56) References Cited

U.S. PATENT DOCUMENTS

| | | | | |
|---|---|---|---|---|
| 4,271,827 | A | 6/1981 | Angelchik | |
| 4,830,003 | A * | 5/1989 | Wolff | A61F 2/86 |
| | | | | 606/191 |
| 5,006,106 | A | 4/1991 | Angelchik | |
| 5,122,154 | A * | 6/1992 | Rhodes | A61F 2/86 |
| | | | | 606/198 |
| 5,980,551 | A * | 11/1999 | Summers | A61L 31/10 |
| | | | | 623/1.42 |
| 6,146,416 | A | 11/2000 | Andersen et al. | |
| 6,432,040 | B1 | 8/2002 | Meah | |
| (Continued) | | | | |

FOREIGN PATENT DOCUMENTS

| | | |
|---|---|---|
| CN | 208404721 U | 1/2019 |
| CN | 209404869 U | 9/2019 |
| (Continued) | | |

OTHER PUBLICATIONS

Invitation to Pay Additional Fees dated Aug. 6, 2021 for International Application No. PCT/2021/031922.

*Primary Examiner* — Suzette J Gherbi
(74) *Attorney, Agent, or Firm* — Seager, Tufte & Wickhem LLP

(57) ABSTRACT

A medical device may include an implantable device for treating a body tissue structure. The implantable device may include a wire structure which may include a wave pattern. The wire structure may be elastic so as to provide a pressure around the body tissue structure such that the pressure may change with movement of the body tissue structure.

22 Claims, 28 Drawing Sheets

(56) References Cited

U.S. PATENT DOCUMENTS

| | | | |
|---|---|---|---|
| 6,517,889 B1* | 2/2003 | Jayaraman | A61P 35/00 |
| | | | 427/232 |
| 6,764,518 B2 | 7/2004 | Godin | |
| 6,773,440 B2 | 8/2004 | Gannoe et al. | |
| 6,960,233 B1* | 11/2005 | Berg | A61F 2/04 |
| | | | 623/23.64 |
| 7,087,088 B2 | 8/2006 | Berg et al. | |
| 7,167,750 B2 | 1/2007 | Knudson et al. | |
| 7,220,237 B2 | 5/2007 | Gannoe et al. | |
| 7,305,993 B2 | 12/2007 | Tropsha et al. | |
| 7,582,110 B2 | 9/2009 | Case et al. | |
| 7,662,087 B2 | 2/2010 | Bailly et al. | |
| 7,695,427 B2 | 4/2010 | Kugler et al. | |
| 7,727,249 B2 | 6/2010 | Rahmani | |
| 7,862,502 B2 | 1/2011 | Pool et al. | |
| 8,123,768 B2 | 2/2012 | Vardi | |
| 8,182,411 B2 | 5/2012 | Dlugos | |
| 8,187,164 B2 | 5/2012 | Kugler et al. | |
| 8,192,349 B2 | 6/2012 | Schurr et al. | |
| 8,282,598 B2 | 10/2012 | Belhe et al. | |
| 8,317,677 B2 | 11/2012 | Bertolote et al. | |
| 8,357,081 B2 | 1/2013 | Nihalani | |
| 8,591,395 B2 | 11/2013 | Ortiz et al. | |
| 9,028,394 B2 | 5/2015 | Honaryar et al. | |
| 9,211,182 B2 | 12/2015 | Errico et al. | |
| 9,526,605 B2 | 12/2016 | Treacy et al. | |
| 9,585,783 B2 | 3/2017 | Meade et al. | |
| 9,801,747 B2 | 10/2017 | Schwab et al. | |
| 9,999,490 B2 | 6/2018 | Rosen et al. | |
| 11,628,052 B2* | 4/2023 | Berg | A61F 5/005 |
| | | | 600/30 |
| 2005/0055082 A1* | 3/2005 | Ben Muvhar | A61F 2/91 |
| | | | 623/1.15 |
| 2005/0125020 A1* | 6/2005 | Meade | A61F 2/848 |
| | | | 606/191 |
| 2006/0089571 A1* | 4/2006 | Gertner | A61F 5/0083 |
| | | | 600/593 |
| 2006/0252983 A1 | 11/2006 | Embo et al. | |
| 2006/0276812 A1 | 12/2006 | Hill et al. | |
| 2007/0142699 A1 | 6/2007 | Jandrall | |
| 2007/0185374 A1 | 8/2007 | Kick et al. | |
| 2007/0249985 A1 | 10/2007 | Brenneman et al. | |
| 2008/0167724 A1* | 7/2008 | Ruane | A61L 31/10 |
| | | | 623/23.7 |
| 2008/0208357 A1* | 8/2008 | Melanson | A61F 5/0076 |
| | | | 623/23.65 |
| 2008/0221595 A1* | 9/2008 | Surti | A61F 5/0079 |
| | | | 606/151 |
| 2008/0249533 A1 | 10/2008 | Godin | |
| 2008/0255587 A1* | 10/2008 | Cully | A61F 5/0076 |
| | | | 606/151 |
| 2008/0319475 A1 | 12/2008 | Clark et al. | |
| 2009/0005857 A1* | 1/2009 | Ischinger | A61F 2/82 |
| | | | 623/1.18 |
| 2009/0012542 A1 | 1/2009 | N'Diaye et al. | |
| 2009/0012546 A1 | 1/2009 | N'Diaye et al. | |
| 2009/0062825 A1 | 3/2009 | Pool et al. | |
| 2009/0093839 A1* | 4/2009 | Kelleher | A61F 2/04 |
| | | | 606/192 |
| 2009/0240268 A1 | 9/2009 | Kassab et al. | |
| 2009/0248142 A1 | 10/2009 | Perkins et al. | |
| 2009/0299486 A1* | 12/2009 | Shohat | A61F 2/04 |
| | | | 623/23.65 |
| 2010/0114327 A1 | 5/2010 | Sobrino-Serrano | |
| 2010/0191271 A1 | 7/2010 | Lau et al. | |
| 2010/0249901 A1 | 9/2010 | Kang | |
| 2010/0280310 A1 | 11/2010 | Raven | |
| 2011/0313240 A1 | 12/2011 | Phillips et al. | |
| 2012/0083819 A1 | 4/2012 | Wang et al. | |
| 2012/0239061 A1* | 9/2012 | Mathur | A61B 17/12013 |
| | | | 606/140 |
| 2013/0018215 A1 | 1/2013 | Snider et al. | |
| 2013/0211189 A1 | 8/2013 | Lau et al. | |
| 2013/0211190 A1 | 8/2013 | Fishler et al. | |
| 2013/0253410 A1* | 9/2013 | Levine | A61F 5/0079 |
| | | | 604/9 |
| 2014/0257462 A1* | 9/2014 | Orion | A61F 2/82 |
| | | | 623/1.15 |
| 2014/0277573 A1 | 9/2014 | Gill et al. | |
| 2014/0309576 A1* | 10/2014 | Belhe | A61F 5/0076 |
| | | | 604/8 |
| 2014/0336696 A1 | 11/2014 | Kugler et al. | |
| 2015/0018855 A1* | 1/2015 | Borkar | A61B 17/1114 |
| | | | 606/154 |
| 2015/0018941 A1* | 1/2015 | Lee | A61F 2/2448 |
| | | | 623/2.37 |
| 2015/0164508 A1 | 6/2015 | Hernandez et al. | |
| 2016/0158051 A1 | 6/2016 | Mische | |
| 2016/0193063 A1 | 7/2016 | St. Germain et al. | |
| 2016/0270934 A1 | 9/2016 | Kitano et al. | |
| 2017/0112650 A1 | 4/2017 | Hingston et al. | |
| 2017/0231694 A1* | 8/2017 | Mathur | A61B 18/1492 |
| | | | 606/41 |
| 2017/0360550 A1 | 12/2017 | Foote et al. | |
| 2018/0325705 A1* | 11/2018 | Harkin | A61F 2/04 |
| 2019/0029795 A1* | 1/2019 | Shelton, IV | A61F 2/0077 |
| 2020/0078158 A1* | 3/2020 | Popescu | A61F 5/0059 |
| 2020/0315823 A1* | 10/2020 | Harkin | A61F 2/848 |
| 2021/0100666 A1* | 4/2021 | Harkin | A61F 2/848 |
| 2021/0186720 A1* | 6/2021 | Bluecher | A61F 2/88 |
| 2021/0298757 A1* | 9/2021 | Forsell | A61B 17/12 |
| 2021/0330443 A1* | 10/2021 | Berg | A61B 17/12013 |
| 2022/0054250 A1* | 2/2022 | Deister | A61B 17/11 |
| 2022/0126012 A1* | 4/2022 | Wolf | A61F 2/064 |

FOREIGN PATENT DOCUMENTS

| | | | |
|---|---|---|---|
| RU | 2286103 | C1 | 10/2006 |
| WO | 2008036352 | A1 | 3/2008 |
| WO | 2008117296 | A1 | 10/2008 |
| WO | 2015195252 | A1 | 12/2015 |
| WO | 2017044929 | A1 | 3/2017 |
| WO | 2019135958 | A2 | 7/2019 |

* cited by examiner

DEVICE FOR USE WITH BODY TISSUE SPHINCTERS

CROSS-REFERENCE TO RELATED APPLICATIONS

This application is a continuation of U.S. patent application Ser. No. 15/931,221, filed May 13, 2020, the entirety of which is incorporated herein by reference.

TECHNICAL FIELD

The present disclosure pertains to medical devices, and methods for manufacturing medical devices. More particularly, the present disclosure pertains to examples of devices for treating body lumens and sphincters, and methods for manufacturing and using such devices.

BACKGROUND

Body sphincters include circular muscles which during normal functioning, maintain constriction of a natural body passage, and relax as needed by normal physiological functioning (e.g., the passage of food, waste, solids, liquid, gasses, etc.) In some cases, body tissue sphincters may lose the ability (e.g., strength, etc.) to maintain constriction of the natural body passage and prevent unintended passage of food, waste, solids, liquids and/or gasses. This can result in, for example, incontinence, heartburn, reflux of colonic contents into the ileum, etc. In some instances, medications, various medical devices, and/or invasive surgeries may be utilized to treat the body tissue sphincter.

SUMMARY

This disclosure provides design, material, manufacturing method, and use alternatives for medical devices. An example medical device may include an implantable device for treating a body tissue structure. The implantable device may include a wire structure which may include a wave pattern. The wire structure may include a singular wire structure which may have a first terminal end and a second terminal end. The first side of the wave pattern may form a flared region relative to a second side of the wave pattern. The wire structure may be elastic so as to provide a pressure around the body tissue structure such that the pressure may change with movement of the body tissue structure.

Alternatively or additionally to any of the embodiments above, the wave pattern may include a plurality of spaced apart loops, and each of the spaced apart loops may provide a smooth, atraumatic end.

Alternatively or additionally to any of the embodiments above, the wire structure may include a closure structure adjacent to the first terminal end and the second terminal end for facilitating forming the prosthetic device into a closed loop.

Alternatively or additionally to any of the embodiments above, the wire structure may be at least partially encapsulated by a coating wherein the coating may promote growth of scar tissue around the body tissue structure.

Alternatively or additionally to any of the embodiments above, the first side of the wave pattern may be encapsulated by the coating to promote growth of scar tissue around the first side of the wave pattern.

Alternatively or additionally to any of the embodiments above, the second side of the wave pattern may be encapsulated by the coating to promote growth of scar tissue around the second side of the wave pattern.

Alternatively or additionally to any of the embodiments above, the wire structure may include the first side having a first spring constant and the second side having a second spring constant different than the first spring constant.

Alternatively or additionally to any of the embodiments above, the first spring constant of the first side may be greater than the second spring constant of the second side.

Alternatively or additionally to any of the embodiments above, the second spring constant of the second side may be greater than the first spring constant of the first side.

Alternative or additionally to any of the embodiments above, the wire structure may be at least partially formed from a bioabsorbable or biodegradable material and may be configured to promote scar tissue at one or more locations at which the wire structure is configured to contact the body tissue.

Another example implantable device for implantation around a body tissue structure may include an annular structure which may have a first terminal end and a second terminal end. The annular structure may be elastic so as to provide a pressure around the body tissue structure such that the pressure may change with movement of the body tissue structure, and the annular structure may include a first side having a first spring constant and a second side having a second spring constant different than the first spring constant.

Alternatively or additionally to any of the embodiments above, the annular structure may be at least partially encapsulated by a coating wherein the coating may promote growth of scar tissue around the body tissue structure.

Alternatively or additionally to any of the embodiments above, the annular structure may include a wave pattern, and the wave pattern may include a plurality of spaced apart loops, wherein each of the spaced apart loops may provide a smooth, atraumatic end.

Alternatively or additionally to any of the embodiments above, the wave pattern may contribute to the first spring constant of the first side and the second spring constant of the second side.

Alternatively or additionally to any of the embodiments above, the first spring constant may be greater than the second spring constant.

Alternatively or additionally to any of the embodiments above, the second spring constant may be greater than the first spring constant.

Another example implantable device for implantation around a body tissue structure may include a wire structure which may include a wave pattern. The wire structure may have a first terminal end and a second terminal end. The wire structure may be elastic so as to provide a pressure around the body tissue structure such that the pressure may change with movement of the body tissue structure. The wire structure may further include a first side having a first spring constant and a second side having a second spring constant different than the first spring constant, and the wire structure may include a closure structure adjacent to the first terminal end and the second terminal end for facilitating forming the implantable device into a closed loop.

Alternatively or additionally to any of the embodiments above, the wire structure may be formed from a single wire.

Alternatively or additionally to any of the embodiments above, the wave pattern may contribute to the first spring constant of the first side and the second spring constant of the second side.

Alternatively or additionally to any of the embodiments above, the wire structure may be at least partially encapsulated by a coating wherein the coating may promote growth of scar tissue around the body tissue structure.

Alternatively or additionally to any of the embodiments above, the wire structure may be at least partially formed from a bioabsorbable or biodegradable material, and the coating may be at least partially formed from a bioabsorbable or biodegradable material.

Alternatively or additionally to any of the embodiments above, the closure structure may include a mechanical latch.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

4

Figure 15:
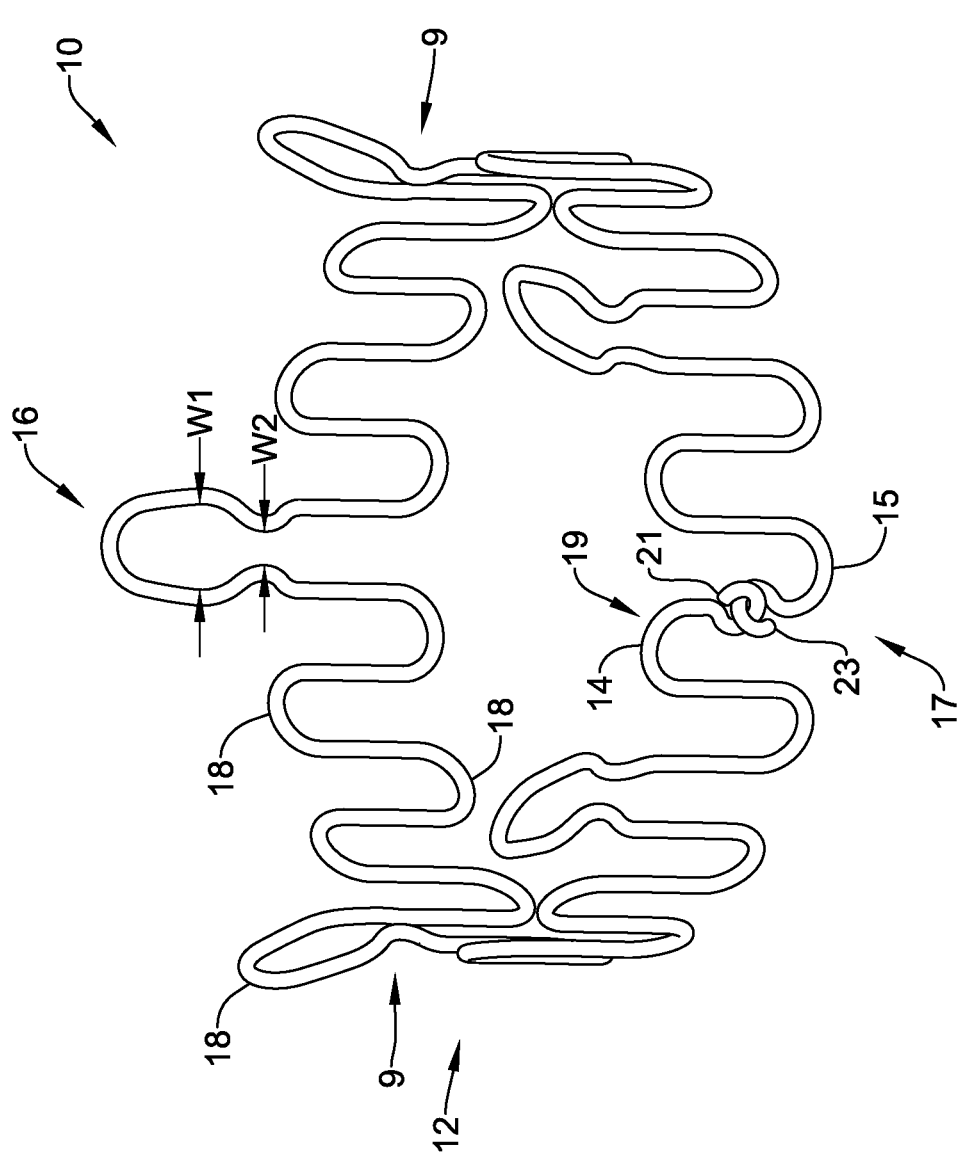
Figure 16:
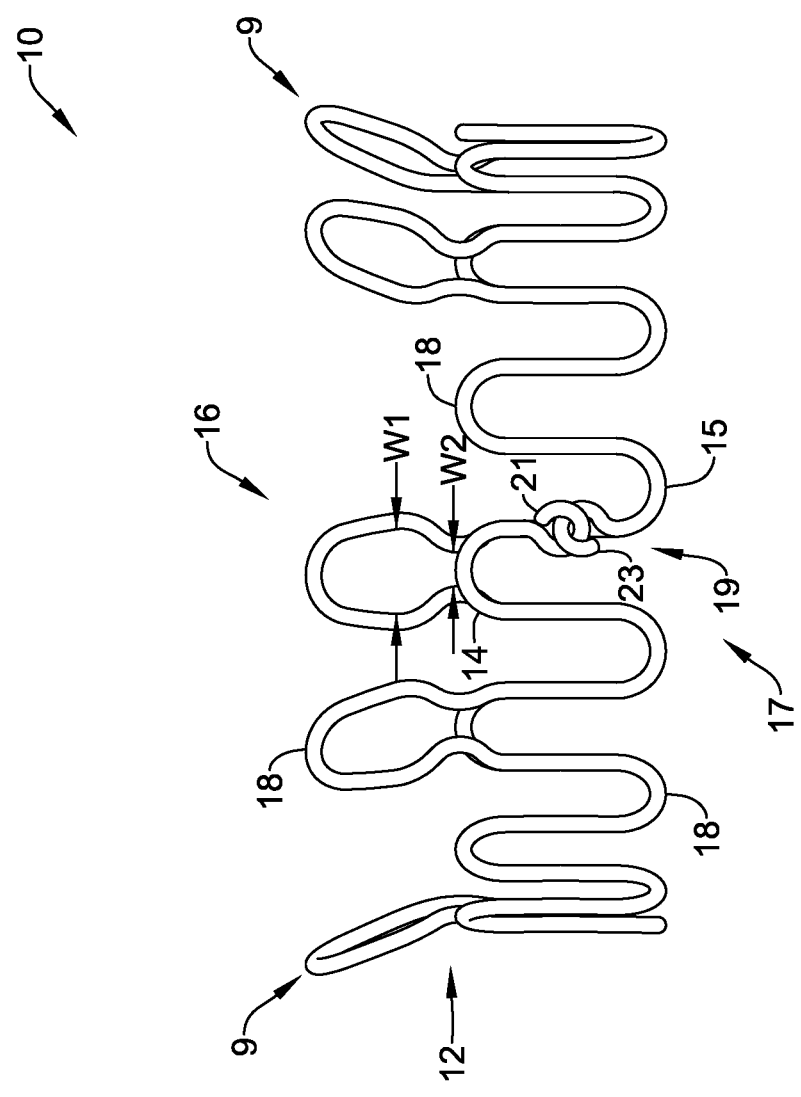
Figure 17:
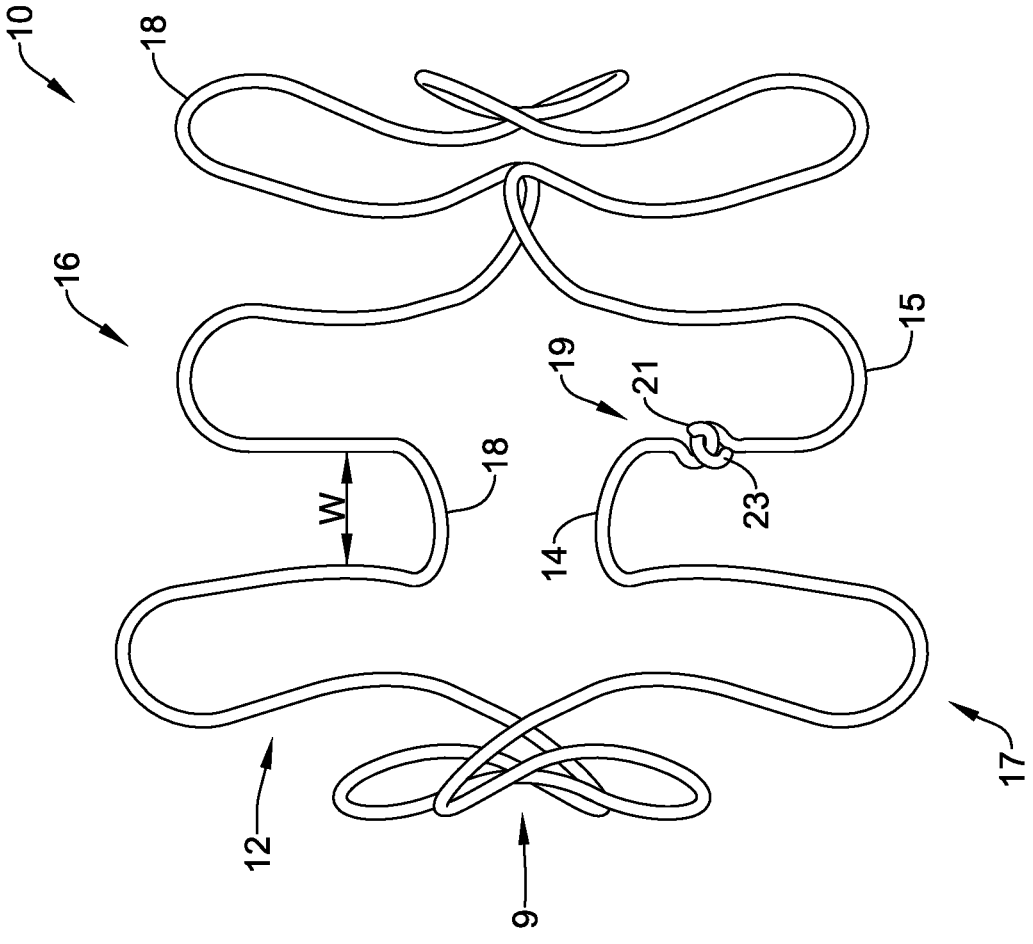
Figure 18:
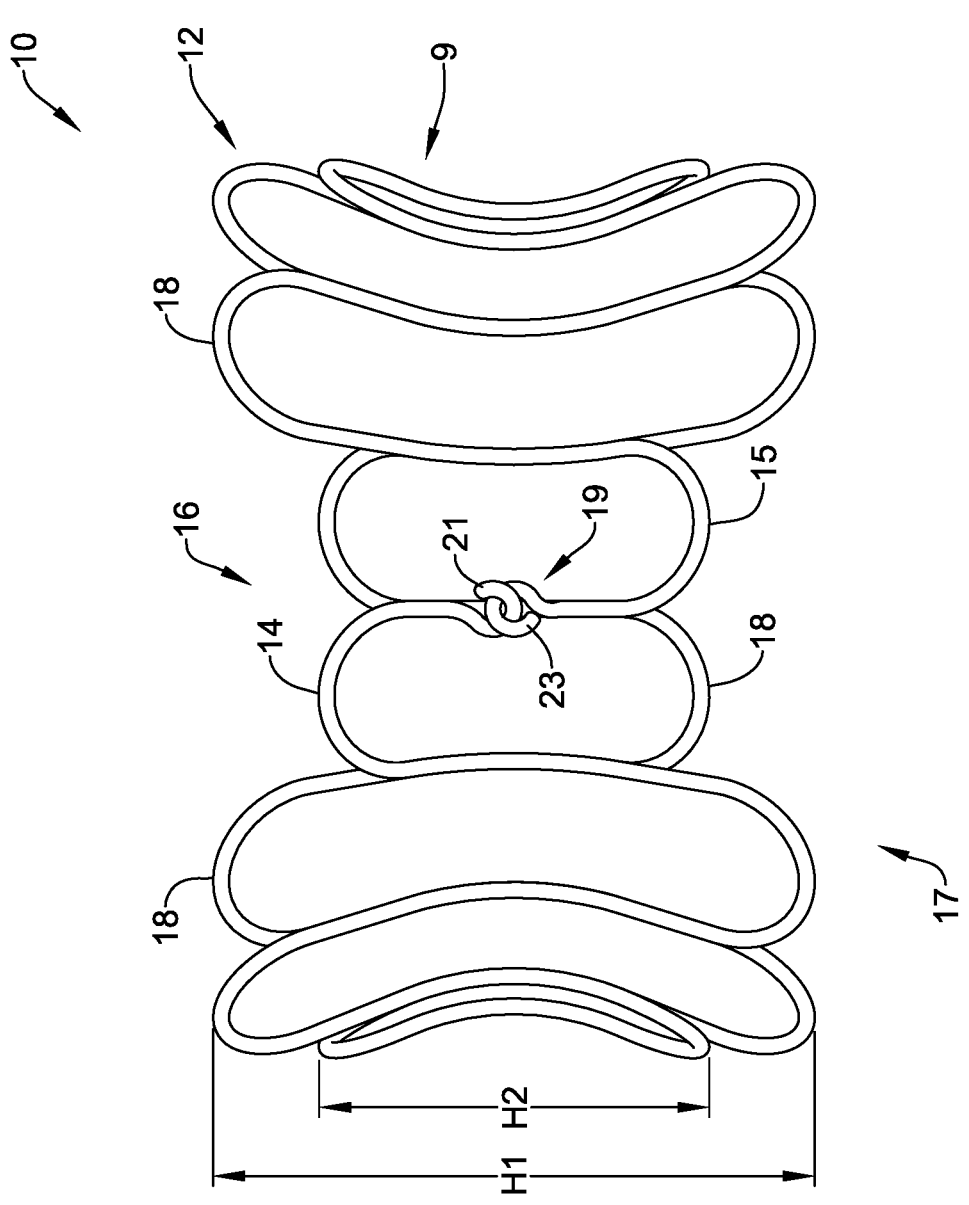
Figure 19:
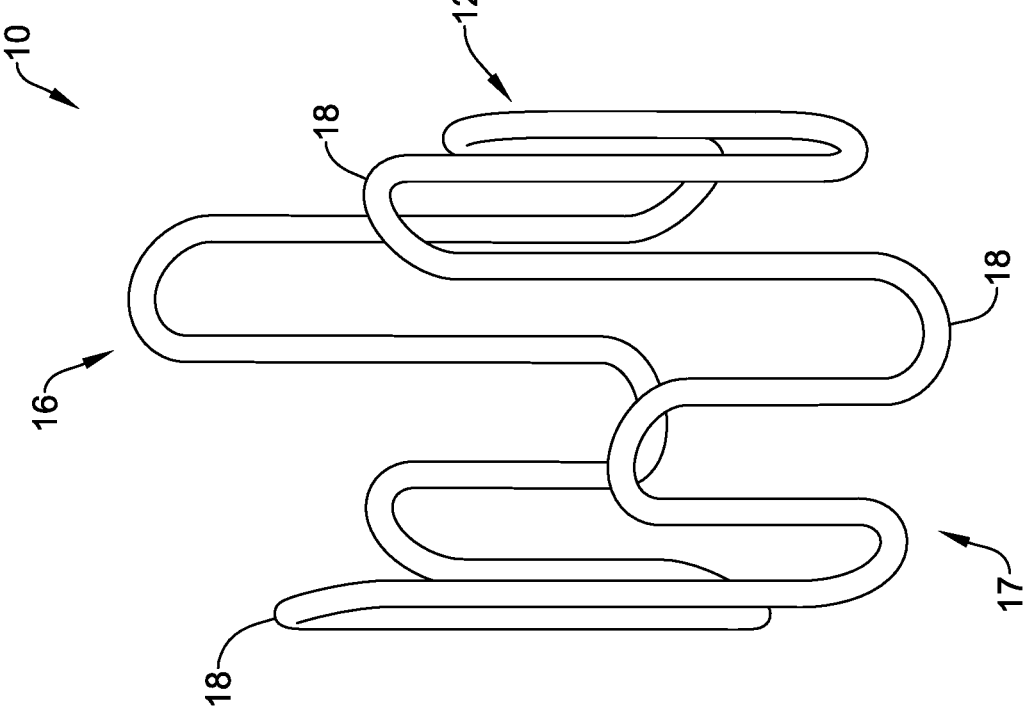
Figure 20:
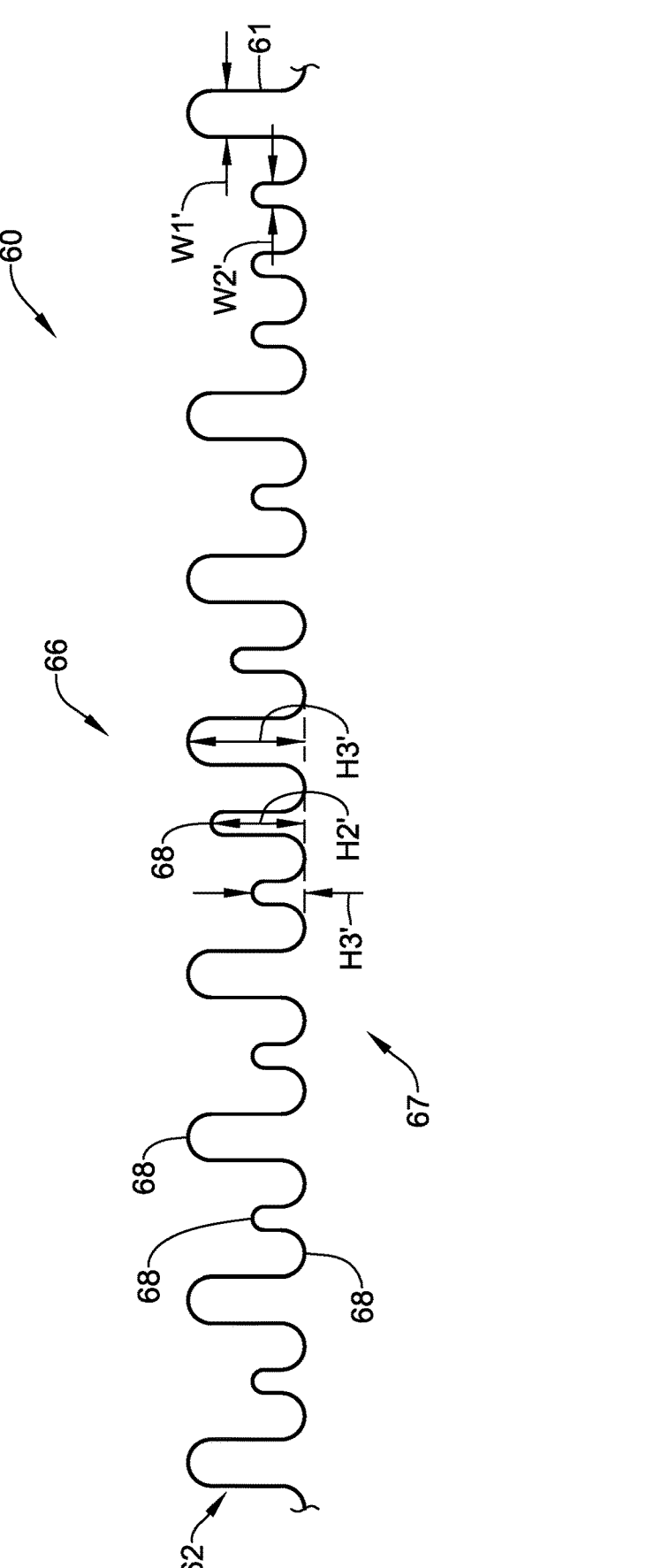
Figure 21:
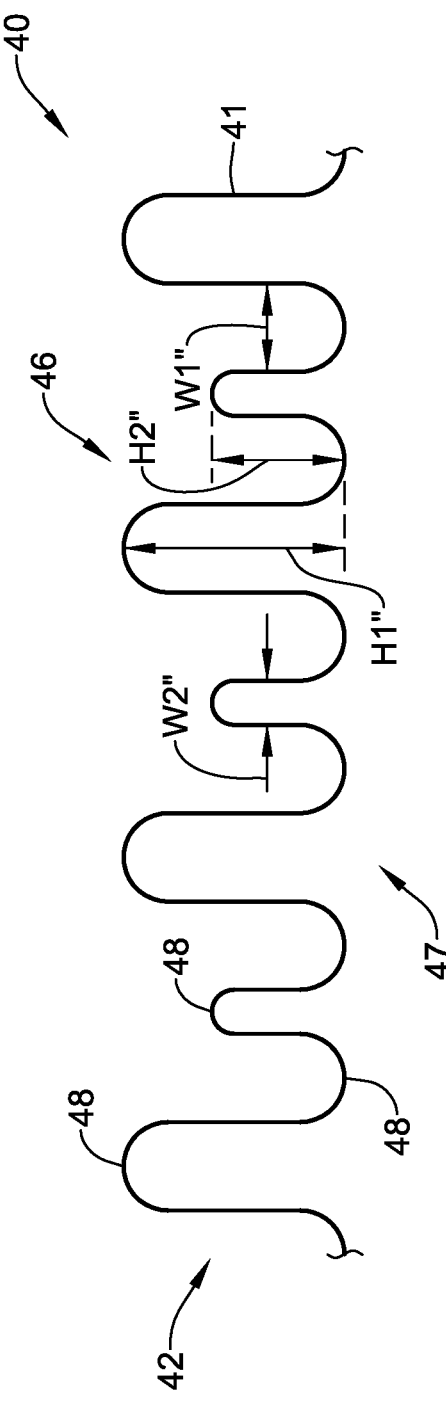
Figure 22:
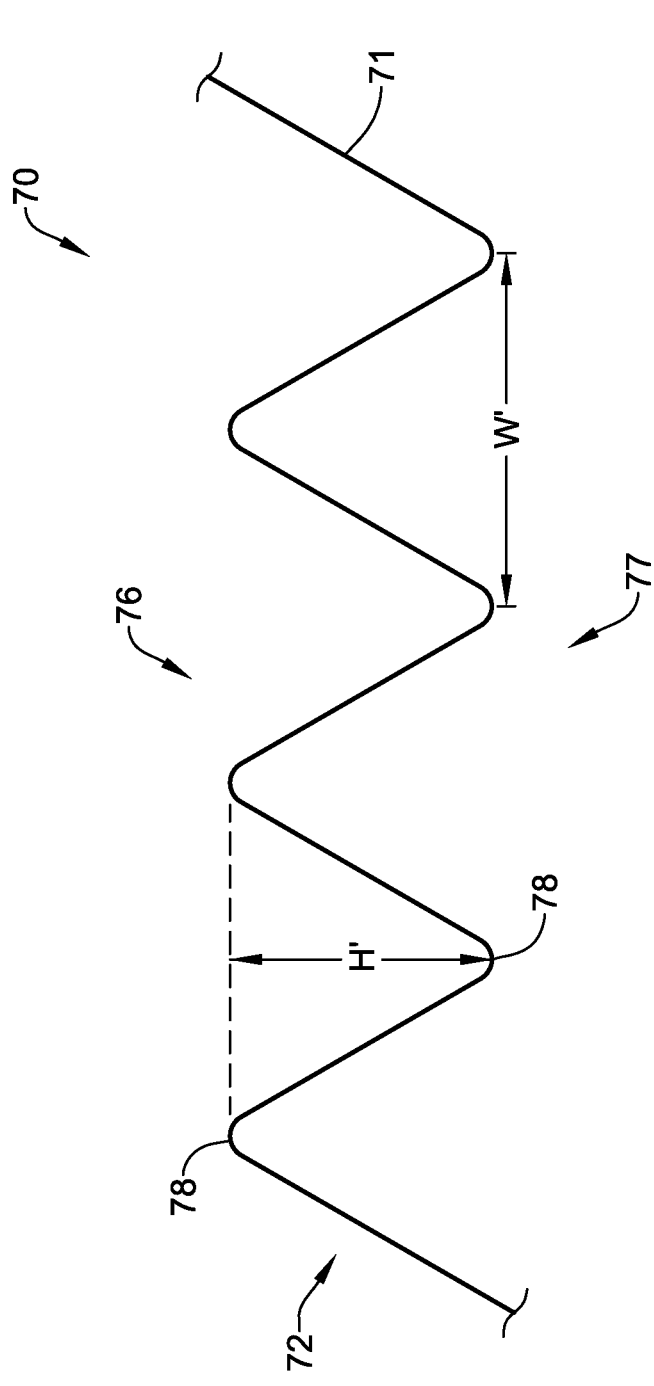
Figure 23:
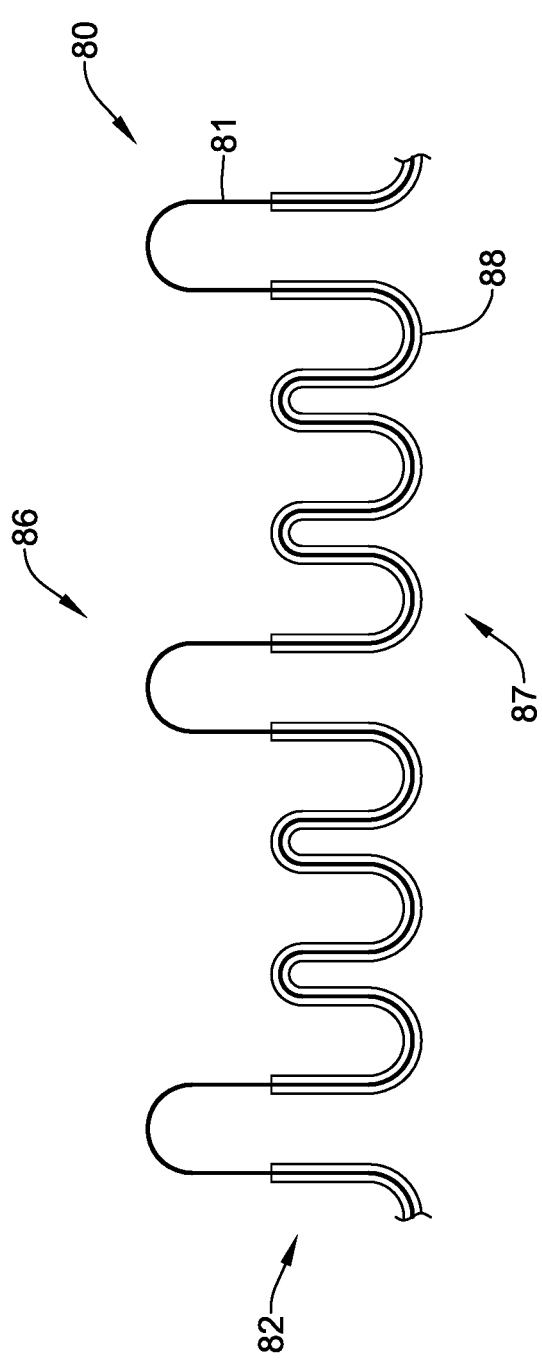
Figure 24:
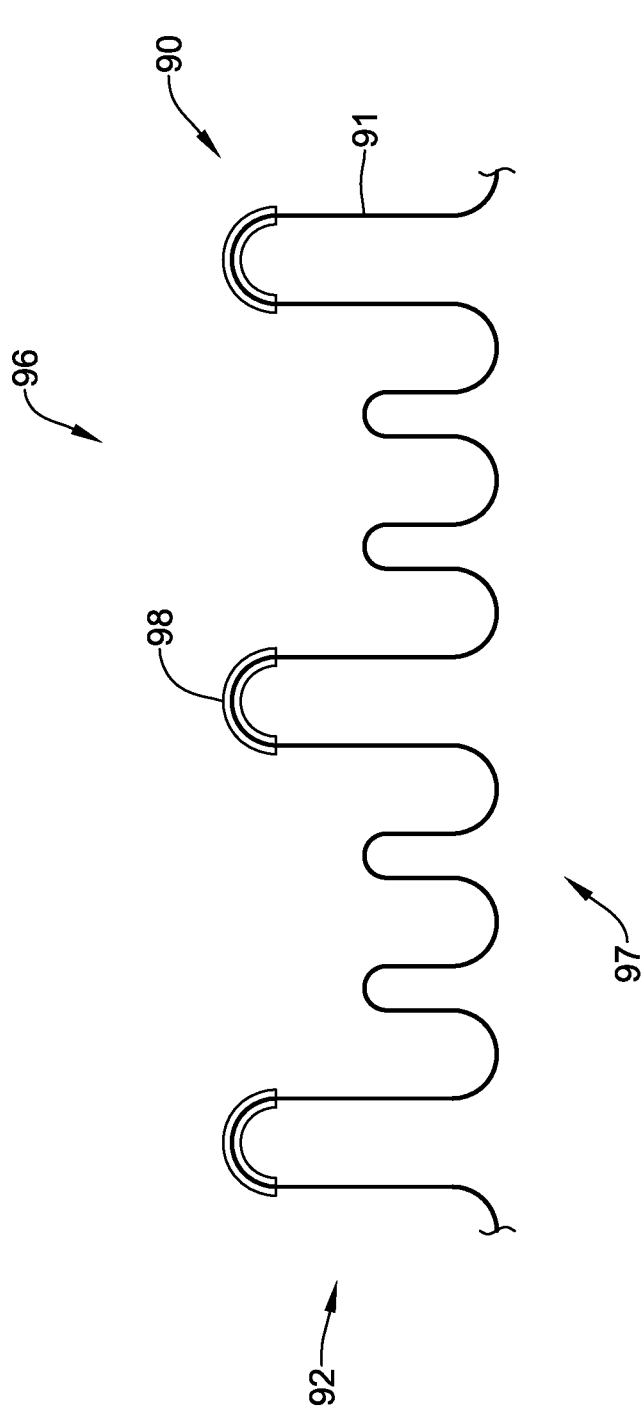
Figure 25:
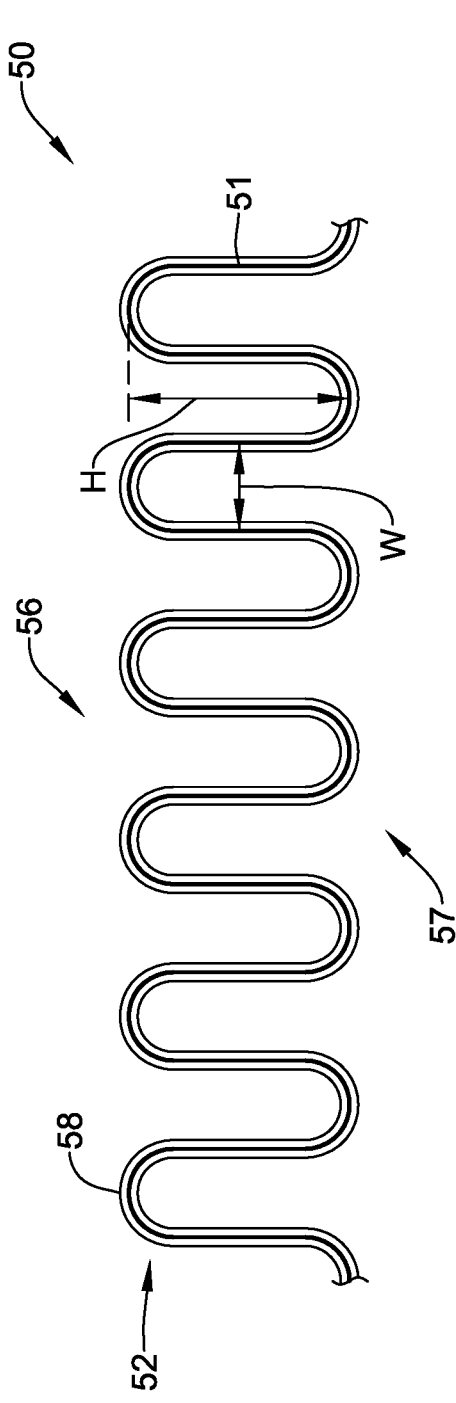
Figure 26:
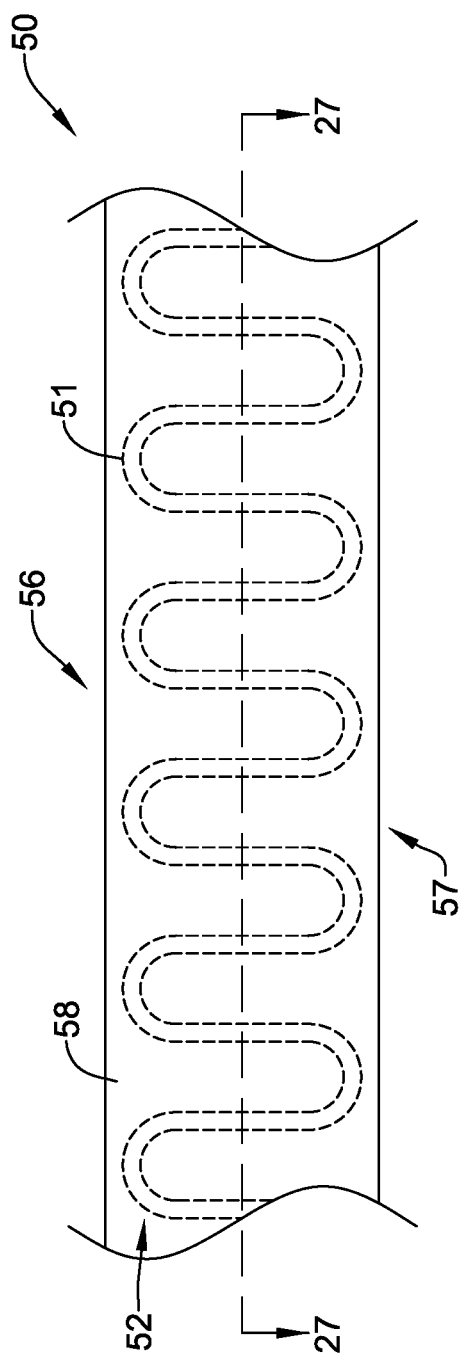
Figure 27:
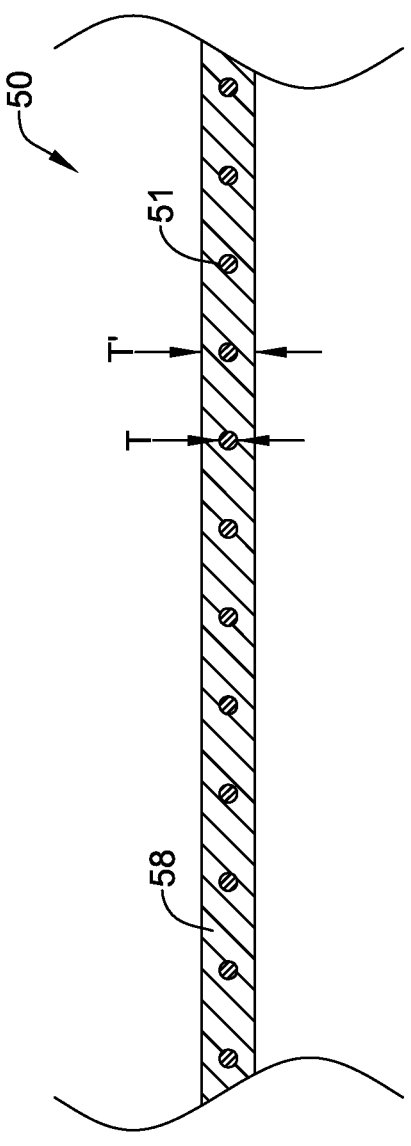
Figure 28:
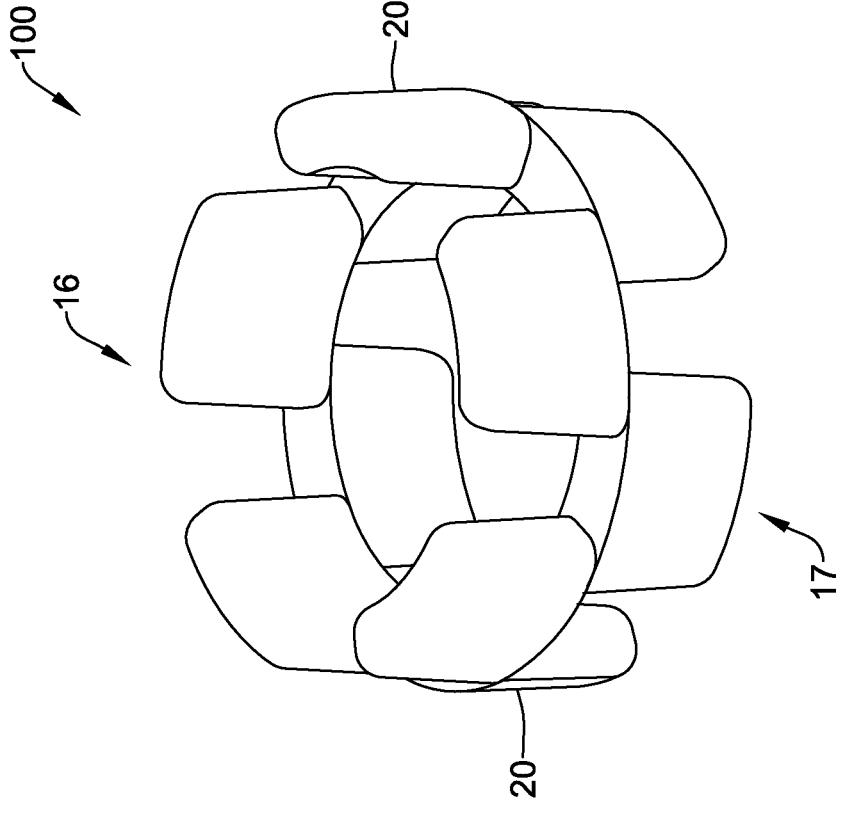

FIG. 15 depicts a schematic perspective view of an illustrative implantable device;

FIG. 16 depicts a schematic side view of the illustrative implantable device depicted in FIG. 15;

FIG. 17 depicts a schematic perspective view of an illustrative implantable device;

FIG. 18 depicts a schematic front side view of the illustrative implantable device, as in FIG. 17;

FIG. 19 depicts a schematic perspective view of an illustrative embodiment of an implantable device;

FIG. 20 depicts a schematic side view of a portion of an illustrative implantable device, the portion being in a planar configuration;

FIG. 21 depicts a schematic side view of a portion of an illustrative implantable device, the portion being in a planar configuration;

FIG. 22 depicts a schematic side view of a portion of an illustrative implantable device, the portion being in a planar configuration;

FIG. 23 depicts a schematic side view of a portion of an illustrative implantable device including a coating, the portion being in a planar configuration;

FIG. 24 depicts a schematic side view of a portion of an illustrative implantable device including a coating, the portion being in a planar configuration;

FIG. 25 depicts a schematic side view of a portion of an illustrative implantable device including a coating, the portion being in a planar configuration;

FIG. 26 depicts a schematic side view of a portion of an illustrative implantable device including a coating, the portion being in a planar configuration;

FIG. 27 depicts a schematic cross-section view of the illustrative implantable device depicted in FIG. 26, taken along line 27-27 in FIG. 26; and FIG. 28 is a schematic perspective view of an illustrative implantable device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

The term "diameter", as used in this specification and the appended claims, is generally employed in its sense as being a line passing from side to side of an object, unless the content clearly dictates otherwise. In some cases, the diameter of an object may pass through a center of the object and/or may be a longest line passing from side to side of the object.

As used in this specification and the appended claims, the singular forms "a", "an", and "the" include plural referents unless the content clearly dictates otherwise. As used in this specification and the appended claims, and although the term "and/or" is sometimes expressly recited herein, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

In some instances, it may be desirable to design an implantable device for implanting around a body sphincter (e.g., a body sphincter of a human, a dog, a horse, and/or other suitable animals) that includes sufficient flexibility to be able to conform to a body vessel/lumen and/or tissue and facilitate normal physiological functioning of the body sphincter or similar physiological functioning adjacent to the body sphincter (e.g., the implantable device may provide sufficient force at or adjacent to the body sphincter to prevent or assist the sphincter in preventing unintended reflux and/or passage of food, waste, solids, liquids, and/or gasses through a body lumen). In some instances, implantable devices designed to be implanted around a body sphincter, such as a lower esophageal sphincter (LES), an intestinal sphincter, or other suitable sphincter, may have a tendency to migrate due to peristalsis (i.e., the involuntary constriction and relaxation of the muscles of the esophagus, intestine, colon, and/or other body lumen that push the contents of the lumen therethrough) and/or migrate for other reasons. Thus, it may be desirable to design a device to be implanted around a body sphincter that promotes growth of scar tissue to help reduce the degree to which the device migrates in addition to further strengthening the sphincter. Examples of implantable devices for treating body tissue sphincters with such capabilities and/or other capabilities are disclosed herein.

Figure 1:
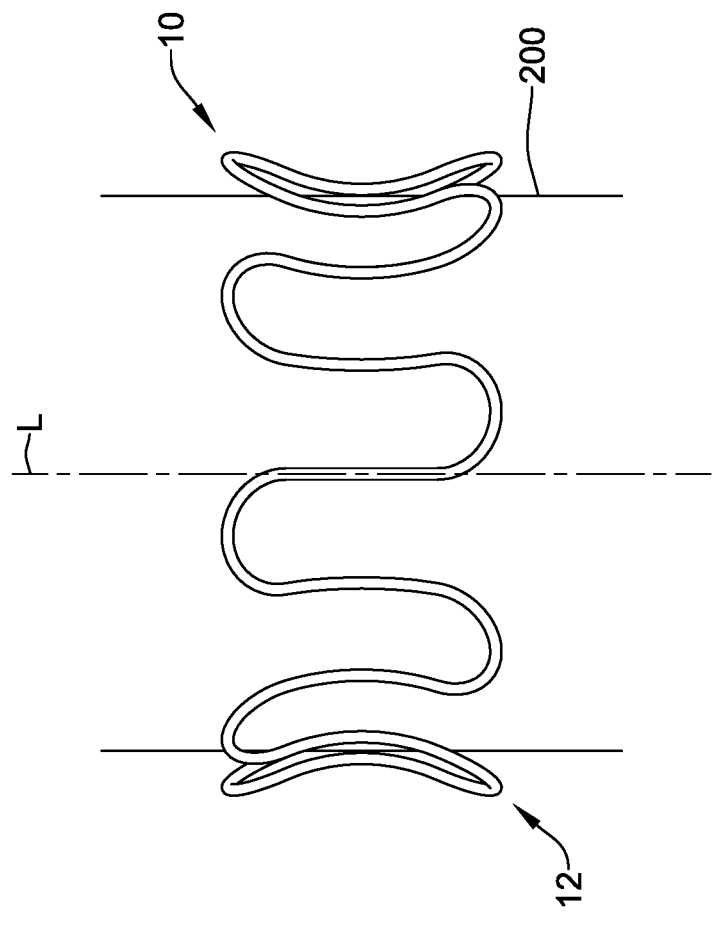
FIG. 1 depicts a schematic side view of an illustrative implantable device shown implanted around a tissue structure in a patient.

FIG. 1 illustrates an implantable device 10 shown implanted around a body tissue 200 of a patient, where the implantable device 10 and the body tissue 200 may extend along a longitudinal axis L. The implantable device 10 may be introduced to a patient and implanted around body tissue of the patient (e.g., a human and/or other suitable animal) through a laparoscopic procedure, a subcutaneous procedure, a percutaneous procedure, a surgical procedure, and/or through one or more other suitable medical procedures.

When the implantable device 10 is configured to be removable or adjustable after implantation, it may be desirable to remove and/or reposition the implantable device 10. In one example removal technique, the implantable device 10 may be removed by gripping a portion of the implantable device 10 and applying a pulling force. In some cases, this may cause the implantable device 10 to straighten from a wave pattern 12 into a linear wire structure, thereby facilitating removal and/or repositioning of the implantable device 10.

The body tissue 200 may be at or adjacent to a sphincter, such as a pyloric sphincter, a urethral sphincter, an anal sphincter (i.e., internal and/or external), a rectal sphincter, an ileocecal sphincter, a lower esophageal sphincter (LES), or the like. The implantable device 10 may be configured to be positioned around a body tissue structure for a variety of medical applications. For example, the implantable device 10 may be used to treat a sphincter in a body (i.e., a human body or an animal body) by facilitating normal physiological functioning of the sphincter thereat and/or similar physiological functioning adjacent thereto. In one example, the implantable device 10 may be implanted around a urethral sphincter and the implantable device 10 may be designed to compress the urethra to prevent urine from passing through the urethra at unintended times.

Figure 2:
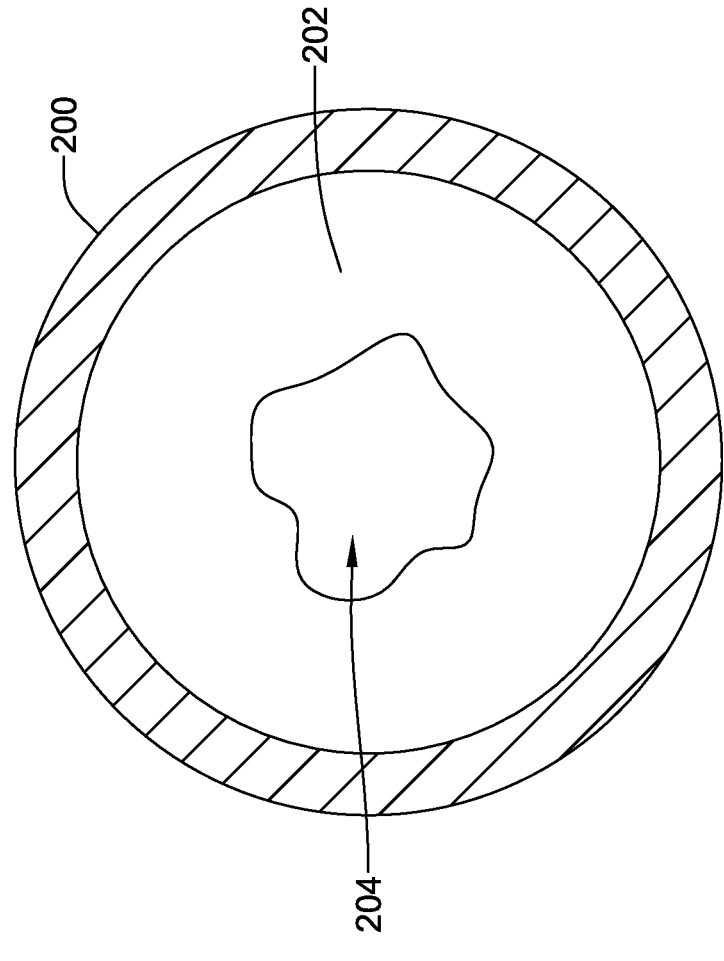
FIG. 2 depicts a schematic cross-section view of a tissue structure in a patient without an illustrative implantable device implanted.
Figure 3:
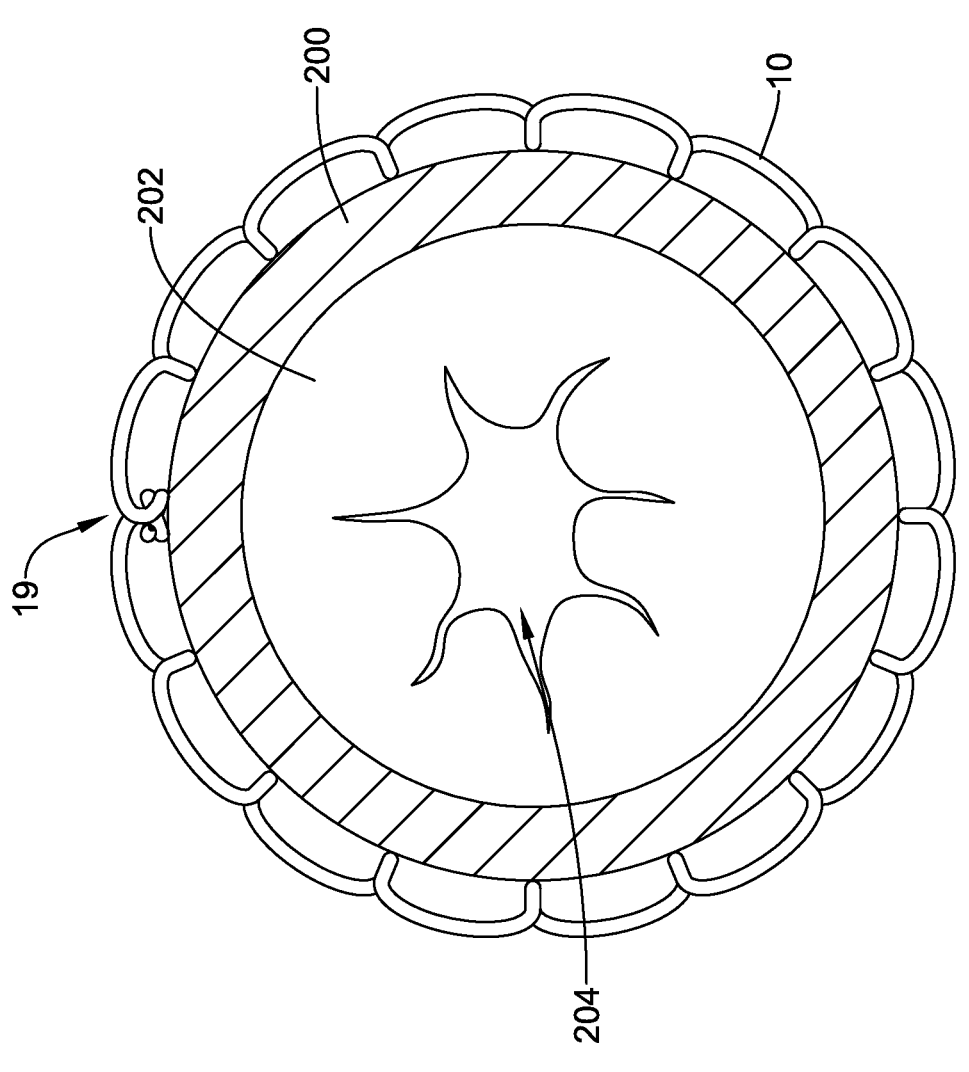
FIG. 3 depicts a schematic cross-section view of the tissue structure in FIG. 2, with an illustrative implantable device implanted.

FIGS. 2 and 3 depict cross-section views taken along the body tissue 200 defining a lumen 204, where the cross-section views include an end view of a sphincter 202. As shown in FIG. 2, the sphincter 202 has been damaged and is not able to properly resist passage of objects and/or fluids (e.g., where objects and/or fluids include fluids, gasses, liquids, and/or solids) moving through the lumen 204. FIG. 3 depicts the body tissue 200 with the implantable device 10, which includes a closure structure 19 (discussed in greater detail below) in the example depicted in FIG. 3, applied thereto at a position at or adjacent to the sphincter 202. With the implantable device 10 implanted around or adjacent to the sphincter 202, the sphincter 202 and the implantable device 10 may work together to resist expansion of the lumen 204 until a radially outward expansion force acting on the body tissue 200 from the lumen 204 reaches a threshold level of force needed to radially expand the implantable device 10. The threshold level of radially outward expansion force needed to expand the implantable device 10 (e.g., where the threshold level of the radially outward expansion force may be a function of a spring constant of the implantable device 10) may be set to match a known and desired force needed to open a properly functioning sphincter 202.

Figure 4:
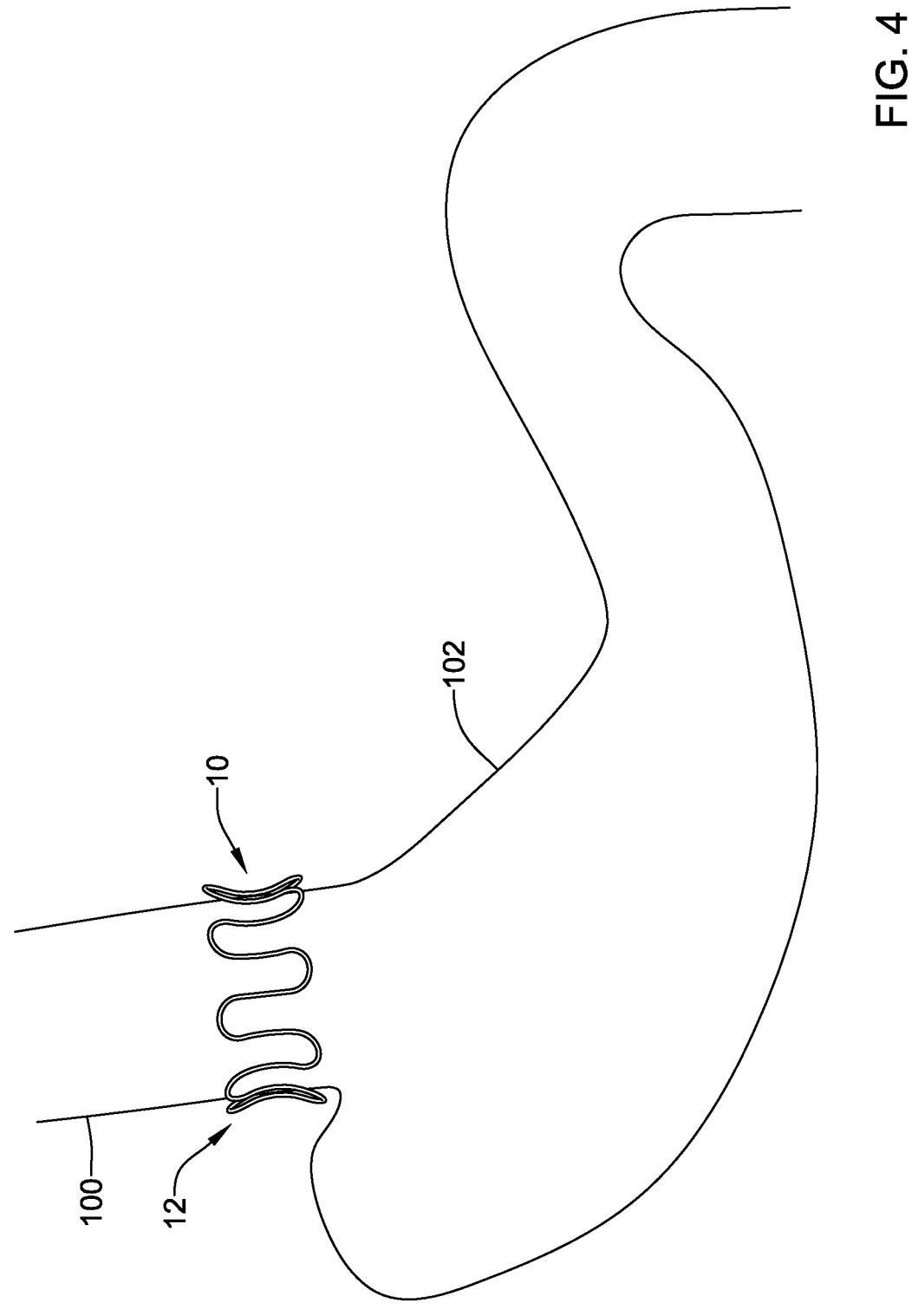
FIG. 4 depicts a schematic side view of an illustrative implantable device shown implanted around an esophagus or body tissue adjacent the esophagus in a patient.

FIG. 4 depicts the illustrative implantable device 10 shown implanted around or adjacent to a lower esophageal sphincter (LES) (e.g., around a body tissue) between an esophagus 100 and a stomach 102. The wave pattern 12 of the implantable device 10 may be formed to allow, when the implantable device 10 is implanted around a LES, passage of food and drink from the esophagus into the stomach and to prevent or limit reflux of food and/or stomach contents back into the esophagus 100 from the stomach 102 that may occur due to gastroesophageal reflux disease (GERD) and/or other diseases or issues. In FIG. 4, the implantable device 10 is shown in its static state, such that an amount of radially inward force from the implantable device 10 acting on the body tissue is equal to the radially outward force from the body tissue acting on the implantable device 10.

Figure 5:
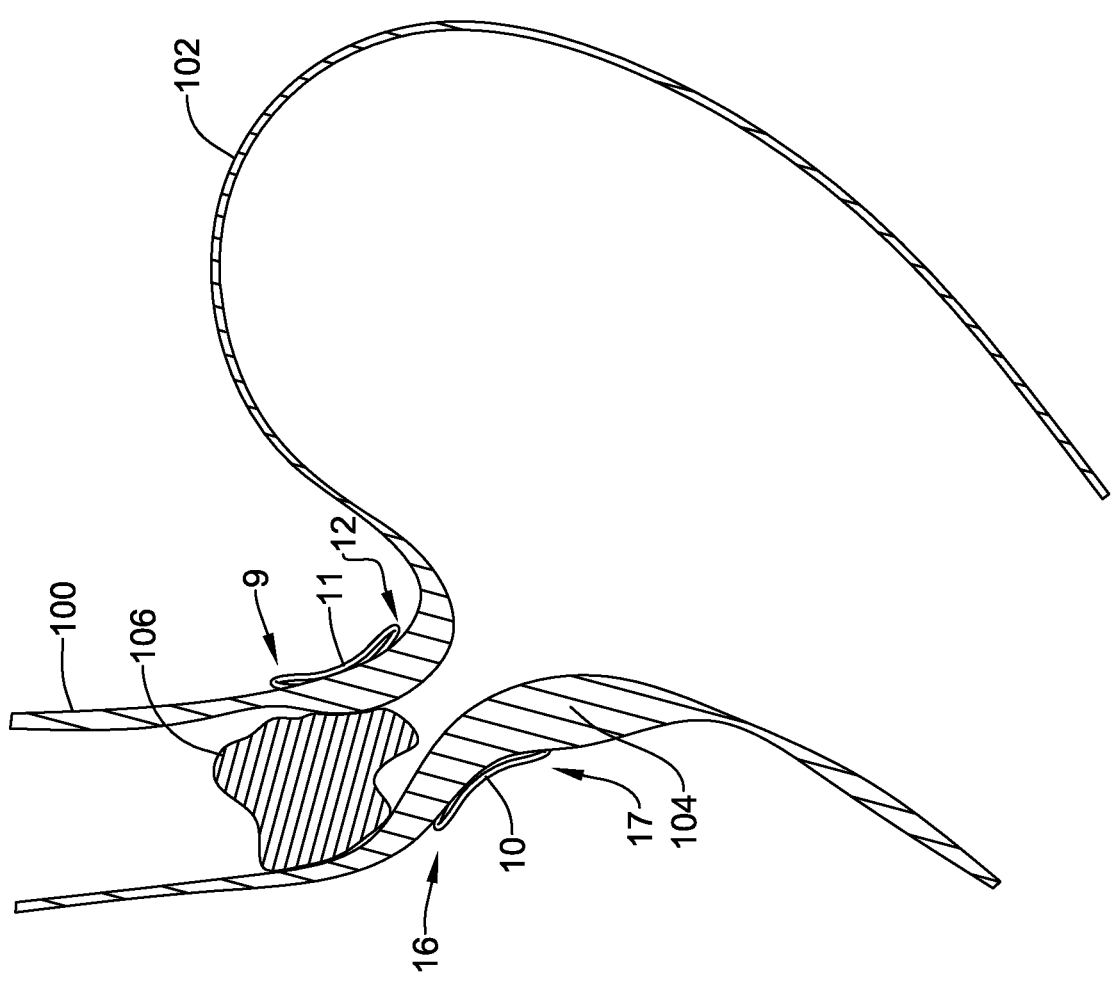
FIG. 5 is a schematic cross-section view of an illustrative implantable device shown implanted around an esophagus or body tissue adjacent the esophagus in a patient, with a bolus traveling therethrough.

FIG. 5 depicts a cross-section view of the illustrative implantable device 10 shown implanted around an LES 104 between the esophagus 100 and the stomach 102. Also shown in FIG. 5, is a bolus 106 (e.g., a bolus 106 of food, liquid, solid, and/or gas) approaching the LES 104 and the implantable device 10. When a patient swallows, the bolus 106 travels from the mouth of the patient through the esophagus 100 to the stomach 102 via peristaltic motion. When the bolus 106 reaches the LES 104, a pressure or force from the bolus 106 acts upon a first side 16 of the wave pattern 12 and the LES 104, overcoming a radially inward force from the LES 104 and the first spring constant of a wire structure 11 associated with the first side 16 of the wave pattern 12 to open the LES 104. The wave pattern 12 may cause the wire structure 11 to have a second spring constant on a second side 17. The second spring constant may be the same as or different than that of the first spring constant, such that the second spring constant may serve to prevent reflux of contents from the stomach 102 back into the esophagus 100 while the first spring constant may be set to easily allow passage of food and drink to the stomach 102. As such, the first spring constant may be less than the second spring constant so as to easily allow the bolus 106 past the implantable device 10, but make it difficult for reflux to cross the implantable device 10. Alternatively or additionally, the first spring constant may be substantially equivalent to the second spring constant.

As discussed, the implantable device 10 may be configured to have a neutral pressure on the esophagus 100 when implanted around the LES 104, such that the implantable device 10 is maintained in its implanted position and does not squeeze or minimally squeezes the esophagus 100 to prevent or mitigate an extent that a lumen through the esophagus 100 is narrowed to a diameter smaller than a natural diameter. In such instances, the spring constants may be set such that a force of or between about ten (10) grams-force to about one hundred twenty-five (125) grams-force, of or between about ten (10) grams-force to about seventy-five (75) grams-force, and/or within one or more other suitable ranges is needed to overcome the spring constant. In one example of an implantable device 10 having a first spring constant and a second spring constant in the manner discussed above, the first spring constant may be set to require about thirty (30) grams-force to overcome the first spring constant and cause the first side 16 of the implantable device 10 to flex outward and the second spring constant may be set to require about fifty (50) grams-force to overcome the second spring constant and cause the second side 17 of the implantable device 10 to flex outward. The spring constant(s) may be configured such that other amounts of force than those discussed above are required to move the implantable device 10 radially outward.

Figure 6:
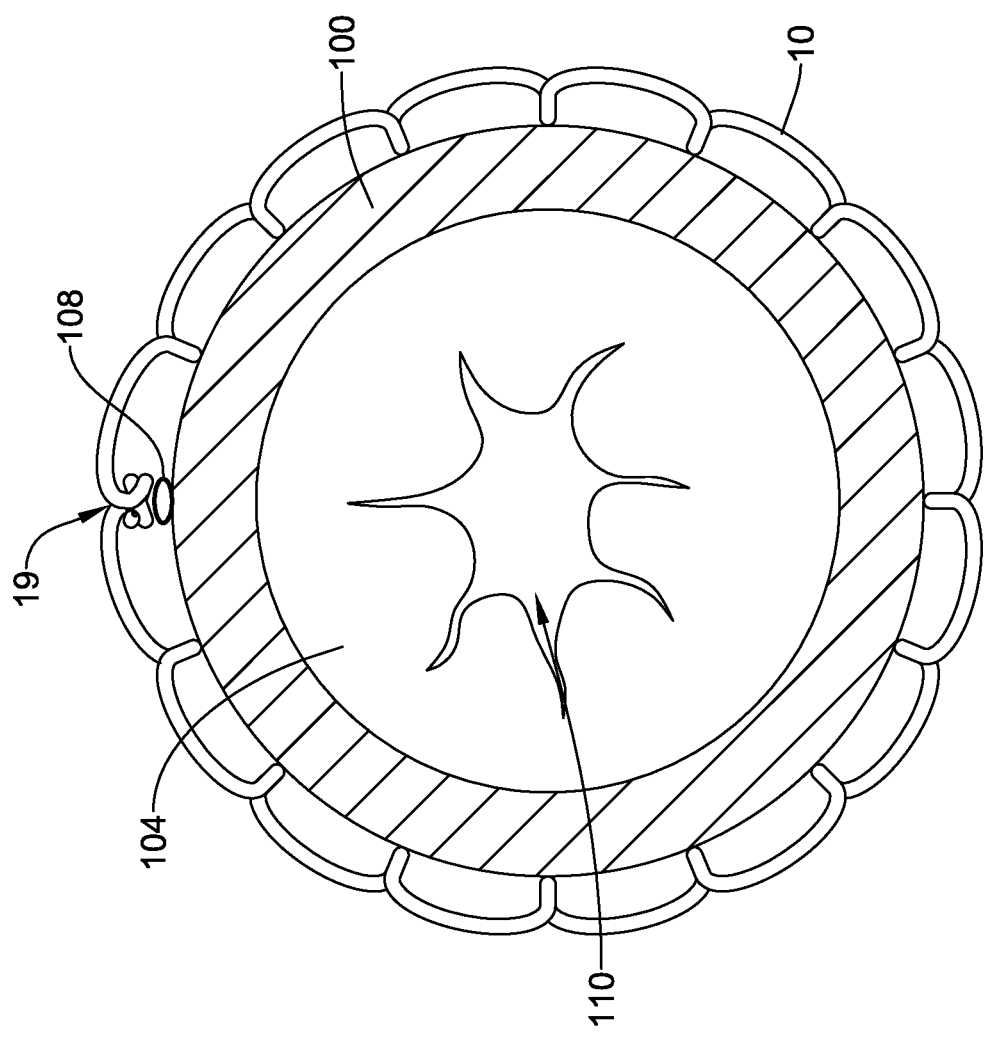
FIG. 6 is a schematic cross-section view of an illustrative implantable device implanted around an esophagus in a patient.

FIG. 6 is a transverse cross-section view taken through the esophagus 100 depicting an end of the implantable device 10 shown implanted around or adjacent to the LES 104 and the esophagus 100. When the implantable device 10 is implanted around or adjacent to the LES 104, the closure structure 19 (discussed in greater detail below) of the implantable device 10 may be designed such that the closure structure 19 fits around a vagus nerve 108 (or other nerve extending along a body tissue to which the implantable device 10 is applied) without applying a pressure or force to the vagus nerve 108. By including the closure structure 19 that fits around the vagus nerve 108, dissection of the vagus nerve 108 is not required. In some cases, the closure structure 19 may not be included.

Figure 7:
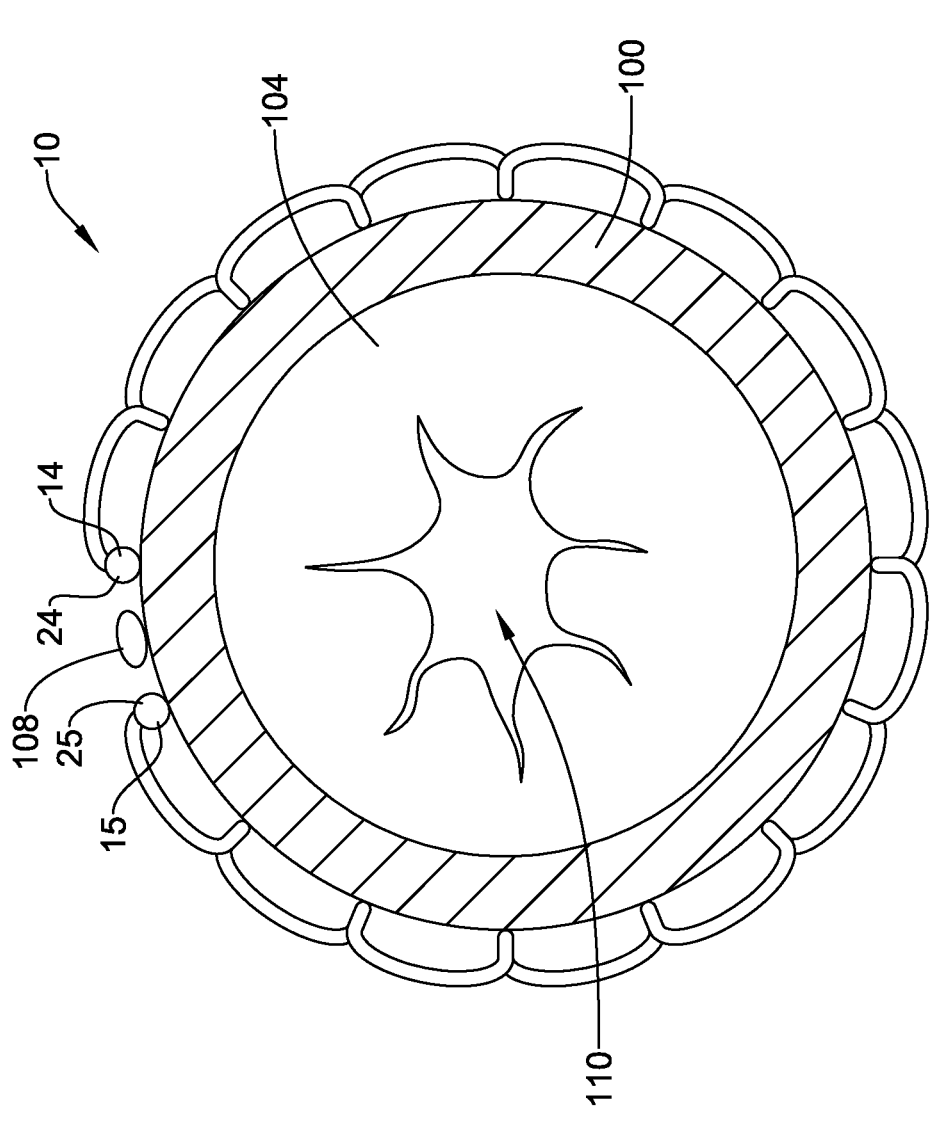
FIG. 7 is a schematic cross-section view of an illustrative implantable device implanted around an esophagus in a patient.

FIG. 7 is a transverse cross-section view taken through the esophagus 100 depicting an end of the implantable device 10 shown implanted around the LES 104 and/or the esophagus 100, similar to as shown in FIG. 6, but where the implantable device 10 does not include the closure structure 19. Rather than utilize the closure structure 19 to maintain the implantable device 10 around the esophagus 100 or body tissue adjacent thereto, the implantable device 10 may have unconnected terminal ends 14, 15 with atraumatic features 25 (e.g., balls or other suitable atraumatic features) formed at the terminal ends 14, 15. In such instances, the radially inward forces applied by the implantable device 10 to the esophagus 100 and/or other body tissue may maintain a desired position of the implantable device 10 around the esophagus 100 and/or around body tissue adjacent thereto. With the configuration of the implantable device 10 depicted in FIG. 7, the implantable device 10 may be positioned around the esophagus 100 and/or other suitable body tissue adjacent thereto such that the vagus nerve 108 is at least partially positioned within a space between the terminal ends 14, 15.

Figure 8:
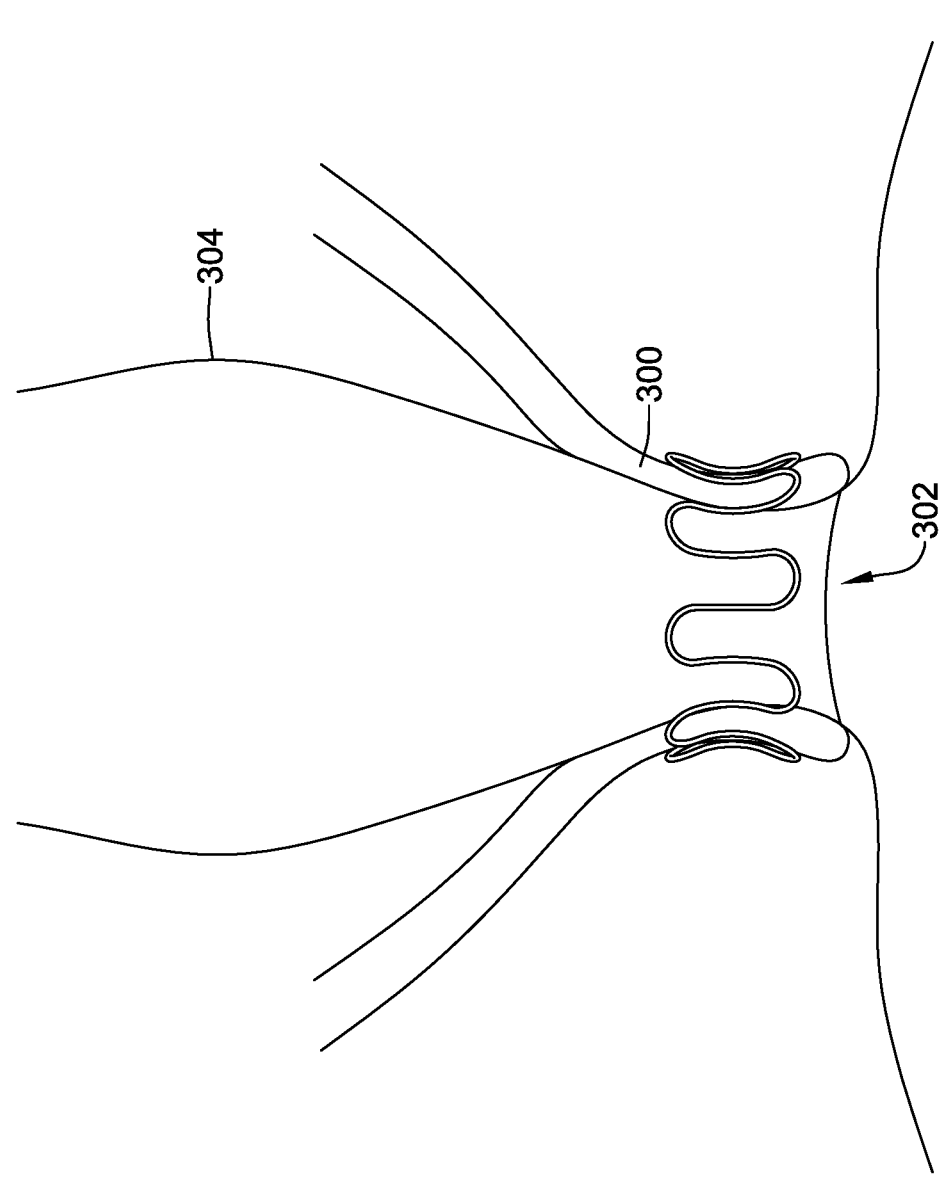
FIG. 8 depicts a schematic side view of an illustrative implantable device shown implanted around an external anal sphincter or body tissue adjacent the external anal sphincter in a patient.

FIG. 8 depicts the illustrative implantable device 10 shown implanted around and/or adjacent to an anal sphincter 300 between an exit of an anal canal 302 and rectum 304 of the patient. The wave pattern 12 of the implantable device 10 may be formed to allow, when the implantable device 10 is implanted around the anal sphincter 300, passage of waste from the rectum out of an exit of the anal canal at intended times, while preventing or at least mitigating inadvertent passing of waste from the rectum 304 to the exit of the anal canal 302 due to a malfunctioning anal sphincter 300 (e.g., due to fecal incontinence). In FIG. 8, the implantable device 10 is shown in its static state, such that an amount of radially inward force from the implantable device 10 acting on the body tissue is equal to the radially outward force from the body tissue acting on the implantable device 10.

Figure 9:
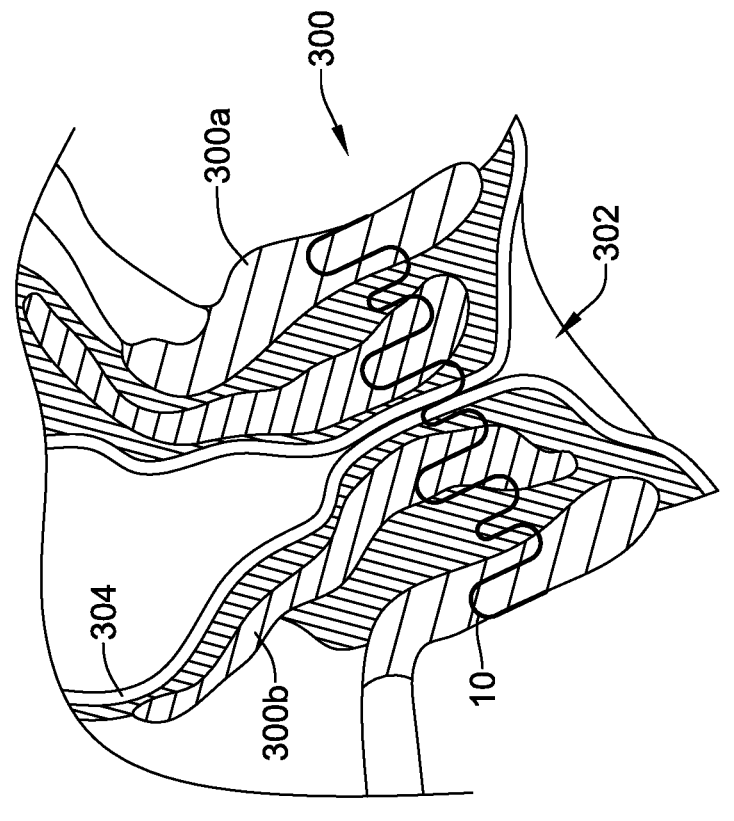
FIG. 9 depicts a schematic cross-section view of an illustrative implantable device shown implanted around an external anal sphincter or body tissue adjacent the external anal sphincter in a patient.

FIG. 9 depicts a cross-section view of the illustrative implantable device 10 shown implanted around the anal sphincter 300 (e.g., around the exterior anal sphincter 300*a* and the internal anal sphincter 300*b*) between the rectum 304 and the exit of the anal canal 302. Although a cross-section view is depicted in FIG. 9 and the implantable device 10 would not typically be depicted with a broken line representing a location of the implantable device around the anal sphincter 300, the implantable device 10 is depicted in FIG. 9 as a solid line for clarity purposes and to depict how the implantable device 10 may function in cooperation with the anal sphincter. As shown in FIG. 9 a radially inward force from the anal sphincter 300 and/or from the implantable device 10 acting on anal sphincter 300 may cause the anal canal 302 to close.

Figure 10:
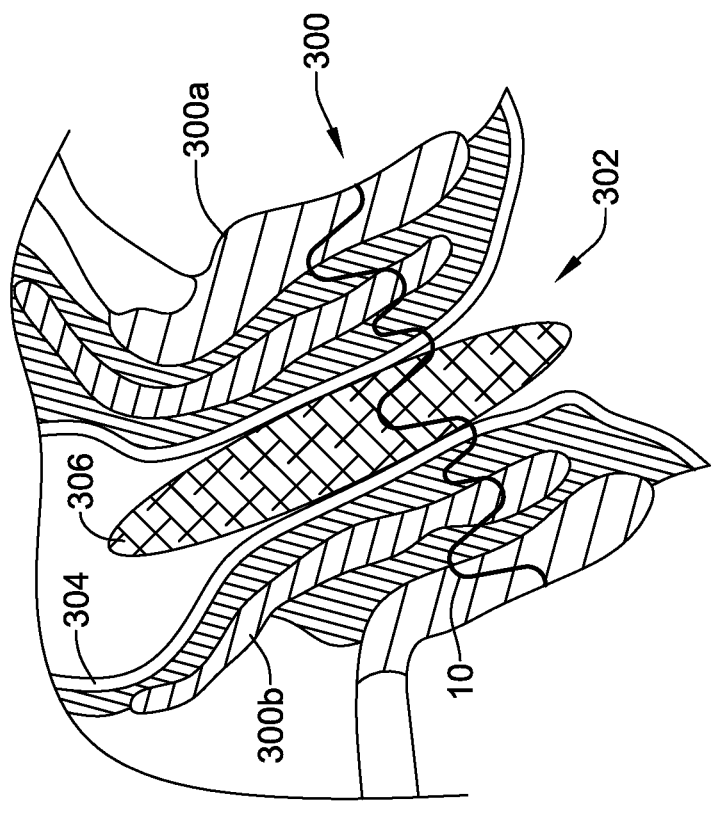
FIG. 10 depicts a schematic cross-section view of an illustrative implantable device shown implanted around an external anal sphincter or body tissue adjacent the external anal sphincter in a patient, with a bolus traveling therethrough.

FIG. 10 depicts a cross-section view similar to the view depicted in FIG. 9, but with a bolus 306 (e.g., a solid, liquid, and/or gas waste bolus) passing through the anal canal 302. When a patient has a bowel movement, the bolus 306 travels from the rectum 304 through the anal sphincter 300 and out the exit of the anal canal 302 via peristaltic motion. When the bolus 306 reaches the anal sphincter 300, a pressure or force from the bolus 306 acts upon the implanted implantable device 10 and the anal sphincter 300, overcoming a radially inward force from the anal sphincter 300 and the implantable device 10 to open the anal sphincter 300 and allow the bolus 306 to exit the anal canal 302. In one example of an implantable device 10 configured to be implanted around the anal sphincter 300, the implantable device 100 may be configured to apply a neutral, resting pressure to the anal sphincter of or between about fifteen (15) mm Hg to about ninety-eight (98) mm Hg and to require a pressure of or between about eighty (80) mm Hg to about three hundred (300) mm Hg. Other suitable pressures are contemplated.

FIGS. 11-28 depict schematic views of illustrative configurations of the implantable device 10. When the implantable device 10 includes the wire structure 11, the wire structure 11 may be configured to have the wave pattern 12 referred to above, but this is not required in all cases and the wire structure may have one or more other suitable configurations. As discussed herein, the wave pattern 12 of the wire structure 11 may take on any suitable design and/or configuration.

Figure 11:
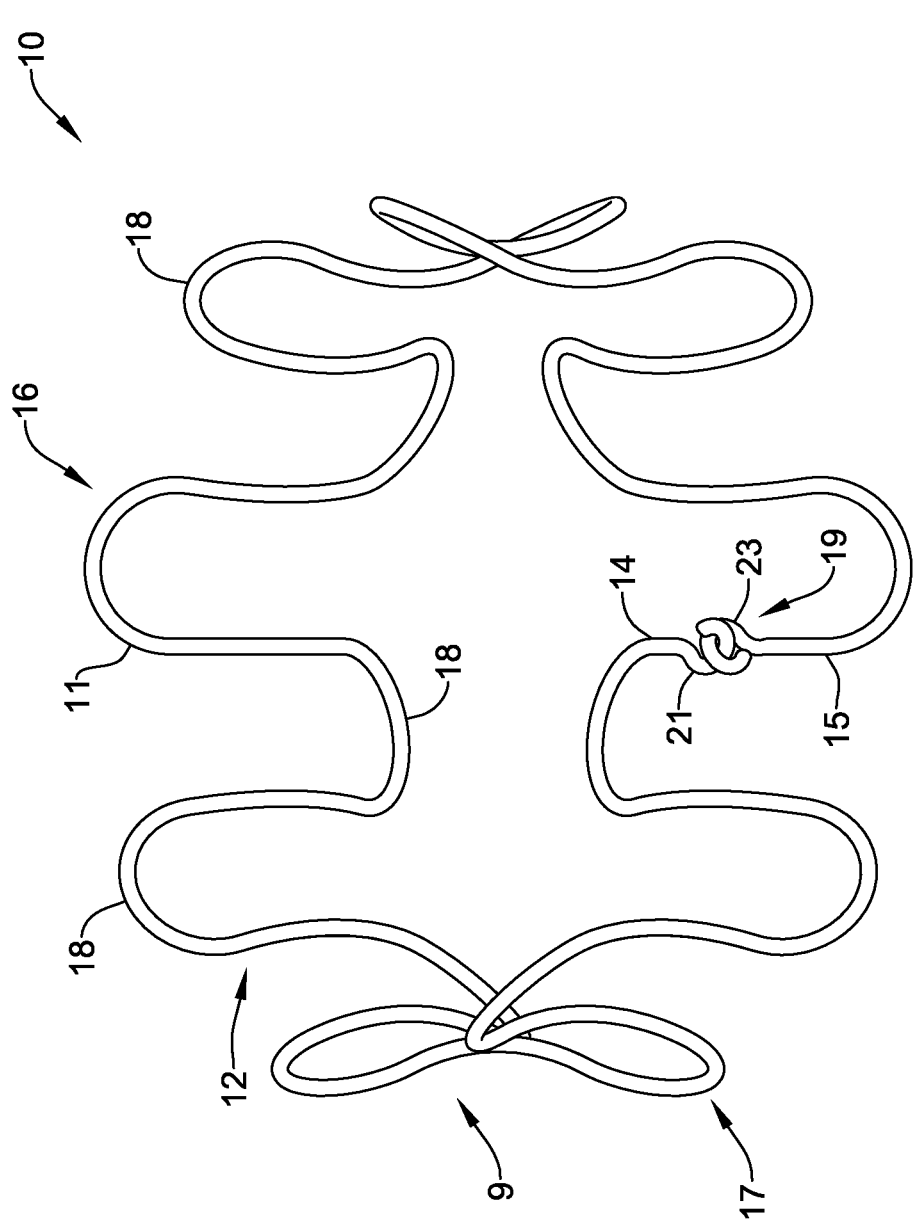
FIG. 11 depicts a schematic perspective view of an illustrative implantable device including a closure structure.
Figure 12:
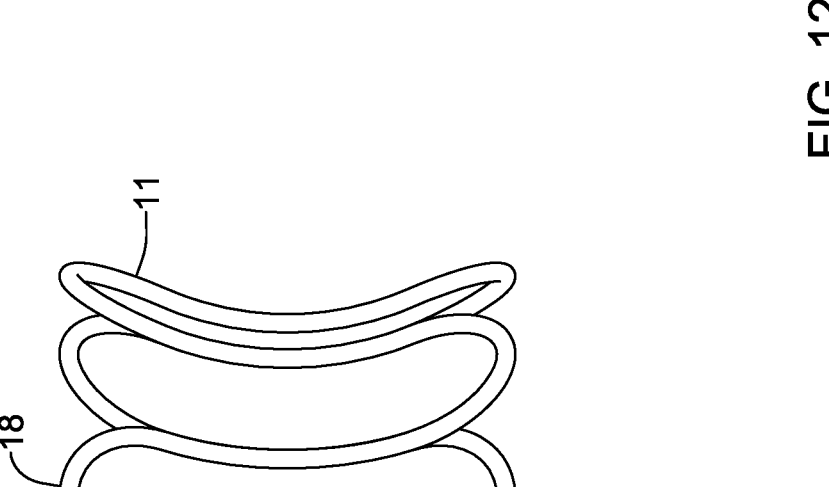
FIG. 12 depicts a schematic side view of the illustrative implantable device including the closure structure, as in FIG. 11.

FIGS. 11 and 12 illustrate schematic views of an illustrative configuration of the implantable device 10 having an annular structure which may be formed into a closed loop with an open interior, via the closure structure 19 that may be positioned adjacent to the first terminal end 14 and the second terminal end 15 of the wire structure 11 (e.g., an expandable, elongate wire structure). The closure structure 19, however, is not required. FIG. 11 depicts the implantable device 10 in a perspective view and FIG. 12 depicts the implantable device 10 in a side view.

Although the closure structure 19, when included, may take one or more various forms for connecting ends of one or more wires forming, at least in part, the implantable device 10, the closure structure 19 may include a loop 21 and a hook 23, as depicted in FIG. 11 for example. Additional or alternative example closure structures include, but are not limited to, a mechanical latch, a magnetic connector, a tubular closure, a snap connector, a suture connector, or the like. In some instances, when the implantable device 10 may be implanted around the LES, the closure structure 19 may be designed such that the closure structure 19 fits around a vagus nerve 108, as shown in FIG. 6 for example.

The elongate wire structure 11 of the implantable device 10 may be formed from a single wire (e.g., as depicted in FIGS. 11 and 12) or may include a plurality of wires connected to form the elongate wire structure 11, where the elongate wire structure 11 may include the first terminal end 14 and the second terminal end 15. In some cases, the wire structure 11 may include a thickness T, as depicted in FIG. 12, which may contribute to a pressure or force (e.g., a radially inward pressure or force) that the implantable device 10 imparts on the body tissue to which the implantable device 10 is applied. In some cases, the thickness T of the wire structure 11 may differ at one or more locations along the wire structure 11 from one or more other locations along the wire structure 11, but this is not required and the wire structure 11 may have a consistent thickness T throughout.

The wire structure 11 of the implantable device 10 and/or other components of the implantable device 10, in at least some examples disclosed herein, may be formed from one or more of a variety of materials configured to flex in response to a force applied thereto and return to a relaxed state when the force is removed. In some cases, components of the implantable device 10 may be formed from a metal (e.g., nickel-titanium alloys, such as nitinol, and/or one or more other suitable metals), a polymeric material (e.g., silicone, PET, and/or one or more other suitable polymers), and/or a combination of metallic and polymeric materials. Additionally, one or more portions of or an entirety of the wire structure 11 and/or the implantable device 10 thereof may include a bioabsorbable and/or biodegradable material (e.g., bioabsorbable and/or biodegradable metals, polymers, and/or other materials including, but not limited to, silk, silicon, plastic, magnesium, etc.). Although not required in all cases, in such configurations the bioabsorbable and/or biodegradable material of the wire structure 11 and/or the implantable device 10 in contact with body tissue may dissolve over a pre-determined period of time and leave scar tissue at locations of contact with the body tissue.

In one example of the implantable device 10, the elongate wire structure 11 may be formed, at least in part, from an elastic material (e.g., nitinol and/or suitable materials having elastic properties). When elastic materials are used to form the wire structure 11 of the implantable device 10, the wire structure 11 may impart the pressure or force (e.g., a radially inward pressure or force) around the body tissue to which the implantable device 10 is applied and may result in changing the movement of the body tissue in response to solids, liquids, and/or gasses passing through a lumen defined by the body tissue such that the body tissue moves and/or functions similar to an adjacent body sphincter.

The wire structure 11 of the implantable device 10 may form the wave pattern 12 which may include a plurality of loops 18 (note, not all loops are labeled for clarity purposes) spaced apart by a width W of adjacent loops 18, as depicted in FIG. 12. One or more of the loops 18 may have a rounded, atraumatic end on the first side 16 of the wave pattern 12 and/or a rounded, atraumatic end on the second side 17 of the wave pattern 12. Alternatively or additionally, one or more of the loops 18 may form a sharp angle that may not be considered atraumatic. In some instances, the first side 16 and/or the second side 17 of the wave pattern 12 may form a flared region 9. For example, FIGS. 11 and 12 illustrate the wire structure 11 forming the first side 16 of the wave pattern 12 having the flared region 9. In some instances, the second side 17 of the wave pattern 12 may form a cylindrical shape having a substantially constant diameter and the first side 16 of the wave pattern 12 may have the flared region 9 flaring radially outward from the substantially constant diameter of the second side 17 (e.g., the flared region 9 may have a diameter that increases from a location adjacent the second side 17 toward the ends of loops 18 on the first side 16, such that the flared region flares radially outward relative to a central longitudinal axis of the implantable device). However, as depicted in FIGS. 11 and 12, the first side 16 and the second side 17 have flared regions. In some instances, the wave pattern 12 may not form a flared region, as shown for example in FIG. 19.

The wave pattern 12 of the implantable device 10 may be and/or may include a geometry designed to provide a contact area with the body tissue that may minimize and/or reduce erosion of the body tissue. The geometry of the wave pattern 12 may include variations in a height, width, radius, thickness, and/or other suitable dimensions of the loops 18 forming the wave pattern 12. Example dimensions of the loops 18 include, but are not limited to, heights of or within a range of about 0.125" to about 1.000", widths of or within a range of about 0.025" to about 0.750", and radii of or within a range of about 0.025" to about 0.750". Other dimensions are contemplated.

Variations in the geometry of the wave pattern 12 may result in variations in a frequency of the loops 18, as shown in FIGS. 14-22 for example, and the geometry and/or frequency of the loops 18 may facilitate providing more or less rigidity to the implantable device 10. For example, including a greater frequency of the loops 18 in the wave pattern 12 may result in a more rigid implantable device 10. In other examples, including a lesser frequency of the loops 18 may result in a less rigid implantable device 10.

Although a geometry and/or a frequency of the loops 18 in the wave pattern 12 may contribute to a rigidity (and thus, a spring constant) of the implantable device 10, other configurations of the wire structure 11 and/or coatings applied thereto may also contribute to the rigidity of the implantable device 10. For example, properties of the material used to form the wire structure 11, a number of wires used to form the wire structure 11, dimensions (e.g., a thickness, shape, etc.) of the wire(s) used to form the wire structure 11, configurations of a wave pattern of the wire(s), and/or other features of the wire structure 11 may contribute to the rigidity of the implantable device 10. In some cases, a desired rigidity of the implantable device 10 and a configuration of the wave pattern 12 may be determined based on the body tissue to which the implantable device 10 is to be applied and intended to treat. For example, an implantable device 10 configured for implanting around the anal sphincter may be configured to apply a higher neutral, resting pressure than a neutral, resting pressure that an implantable device 10 configured for implanting around the esophagus may be configured to apply.

The geometry (e.g., configuration) of the wave pattern 12 of the implantable device 10 may facilitate preventing migration of the implantable device 10 by promoting growth of scar tissue around the implantable device 10. For example, a wave pattern 12 having larger, less frequent loops 18 relative to smaller, more frequent loops 18 may promote an increased growth of scar tissue, as opposed to expected scar tissue that results from the smaller, more frequent loops 18. In addition to anchoring the implantable device 10 in place, the progressive growth of scar tissue over time may thicken the body tissue to which the implantable device 10 is applied and may increase the performance of the implantable device 10 by allowing the body tissue structure to slowly adjust to the presence of the implantable device 10, and further help control the normal functions of the body tissue (e.g., LES, urethral sphincter, anal sphincter, or the like).

Figure 13:
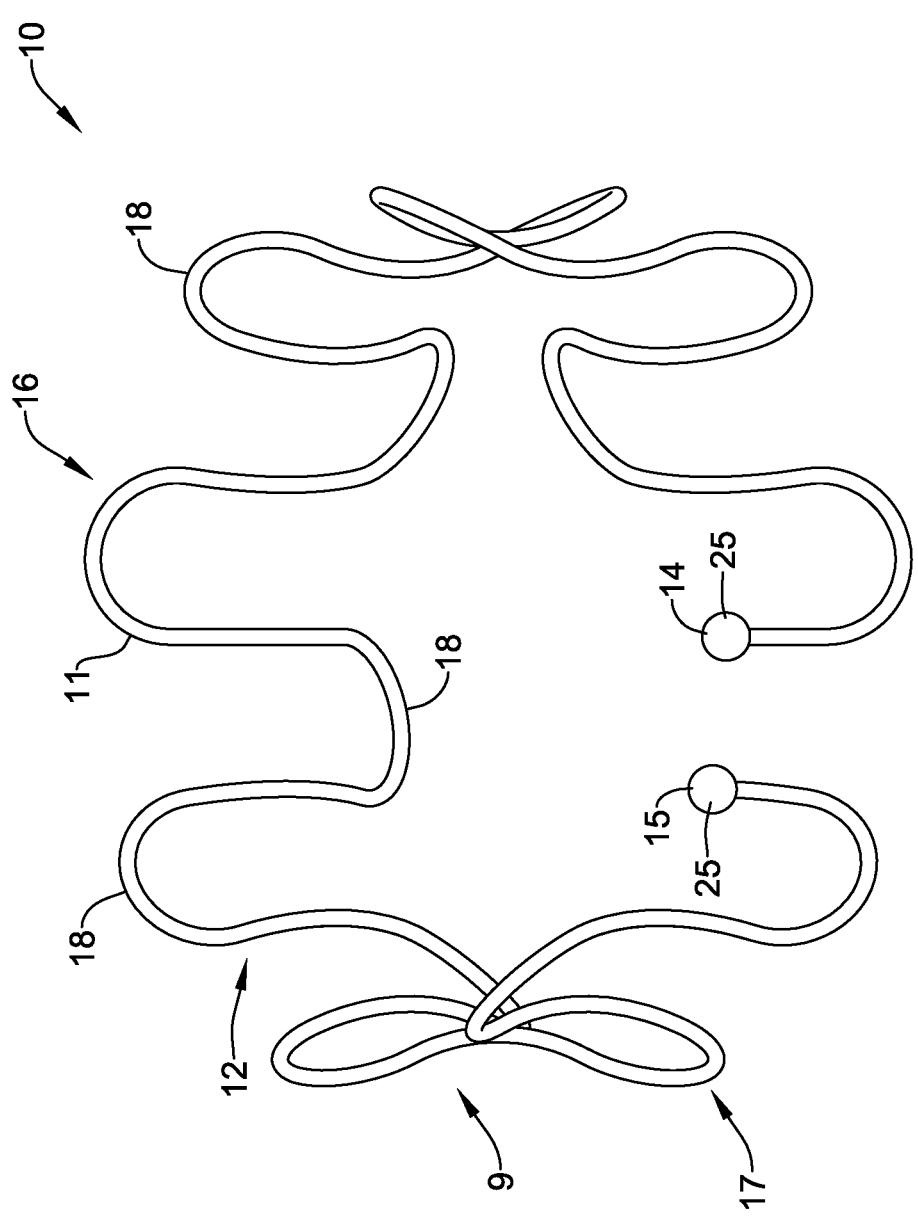
FIG. 13 depicts a schematic perspective view of an illustrative implantable device.

As shown in FIG. 13, the closure structure 19 may be omitted from the implantable device 10. In this manner, the implantable device 10 may be designed in a C-clamp or similar fashion where the terminal ends 14 and 15 of the wire structure 11 are not connected and the spring constant of the wire structure 11 in combination with an annular shape of the wire structure 11 facilitate maintaining the implantable device 10 around a body structure when implanted there around. Further, the implantable device 10 without the closure structure 19 may include a coating on the wire structure 11 to promote the growth of scar tissue and hold the implantable device 10 in place. In some instances, when the implantable device 10 may be implanted around the lower esophageal sphincter, an opening provided between the first terminal end 14 and the second terminal end 15, when the opening is included, may be designed such that the opening fits around the vagus nerve. The implantable device 10 may be similarly implanted around other body tissue so as to avoid contact with other anatomical features extending along the body tissue.

When the terminal ends 14, 15 of the wire structure 11 are free of the closure structure 19, and/or in other configurations, the terminal ends 14, 15 may include atraumatic features to prevent undesirable puncturing of body tissue. In one example, the wire structure 11 may be formed with atraumatic, rounded or ball-shaped terminal ends 25 that may be attached to or formed from the material forming the wire structure 11.

FIGS. 14-22 illustrate additional configurations of the implantable device 10 including various configurations of wave patterns 12. The various wave patterns 12 may be configured for one or more purposes, including, but not limited to, facilitating setting spring constants at the first side and/or the second side of the implantable device 10, promoting scarring at particular locations long body tissue (e.g., designer scarring), and/or configured for one or more other suitable purposes. In one example, the first side 16 of the wave pattern 12 may have less frequent loops 18 than the second side 17 of the wave pattern 12, such that a spring constant of the implantable device 10 at the second side 17 of the wave pattern 12 may require more force to cause expansion of the implantable device 10 and allow the passage of solids, liquids, and/or gasses entering the implantable device 10 from the second side 17 of the wave pattern 12 than a force caused by a spring constant of the implantable device 10 at the first side 16 of wave pattern 12 that is required to cause expansion of the implantable device 10 in response to solids, liquids, and/or gasses entering the implantable device 10 from the first side 16 of the wave pattern 12. In some instances, such as, for example, when the implantable device 10 may be implanted around the lower esophageal sphincter, it may be desirable to include a wave pattern 12 having more frequent loops 18 at the second side 17 of the wave pattern 12 of the implantable device 10 to provide a spring constant requiring more force to cause expansion of the implantable device 10 so as to prevent unintended passage of solids, liquids, and/or gasses from the stomach back into the esophagus, and less frequent loops 18 on the first side 16 of the wave pattern 12 of the implantable device 10 to provide a spring constant that requires lower or typical force to allow the passage of solids, liquid, and/or gasses from the esophagus into the stomach. This is just an example.

The various wave patterns 12 of the wire structure 11 may be configured to promote growth of scar tissue around the implantable device 10 (e.g., thickening of body tissue at and/or around the wire structure 11). As scar tissue may grow around the implantable device 10 where the implantable device 10 contacts body tissue, the wave pattern 12 of the wire structure 11 of the implantable device 10 may be configured to promote scar tissue growth at desired locations (e.g., at one or more locations) around and/or along the body tissue. Such promotion of scarring by configuring and/or particularly designing the wave pattern 12 of the wire structure 11 may be referred to as "designer scarring".

In some instances, it may be desirable to promote the growth of scar tissue in a specific pattern around the body tissue structure. For example, when the implantable device 10 may be implanted around the lower esophageal sphincter, it may be desirable to promote the growth of scar tissue such that the scar tissue may form a "funnel" shape (e.g., a denser scar tissue pattern adjacent a distal side of the implantable device 10 nearer a stomach than a scar tissue pattern adjacent a proximal side of the implantable device 10). In the example, the wave pattern 12 may include less frequent loops 18 on the first side 16, and more frequent loops 18 on the second side 17. This is just an example. Although various wave patterns are depicted in FIGS. 14-22, other suitable wave patterns for the implantable device 10 are contemplated.

When the implantable device 10 is formed from a bioabsorbable and/or biodegradable material, the implantable device 10 may be configured to form scar tissue (e.g., the designer scar tissue and/or other suitable scar tissue) along the body tissue such that once the bioabsorbable and/or biodegradable material absorbs and/or degrades, the remaining scar tissue facilitates operation of a sphincter in a manner similar to as when the implantable device 10 was located around the body tissue, as discussed herein. For example, the scar tissue remaining after the implantable device 10 has absorbed and/or degraded may cause the body tissue to be more or less expandable, flexible, and/or pliable based on locations of the scar tissue, which may facilitate control of flow through a lumen defined by the body tissue without leaving a long term implant around the body tissue. In one example in which the implantable device 10 is implanted at or adjacent to the lower esophageal sphincter, a distal end (e.g., nearer a stomach than a proximal end) of the scar tissue remaining after the implantable device 10 has absorbed and/or degraded may be configured to be more dense at one or more locations along a circumference of the esophagus than at one or more locations along a circumference of the esophagus at the proximal end of the scar tissue to facilitate passage of solids, liquids and/or gasses from the esophagus into the stomach and prevent/limit passage of solids, liquids and/or gasses from the stomach into the esophagus. Although the distal scar tissue and/or the distal end of the implantable device 10 are discussed as being configured to make it more difficult for body tissue to expand (e.g., configured to provide more resistances to expansion) than the proximal scar tissue and/or the proximal end of the implantable device 10, the scar tissue and/or the implantable device 10 may be configured such that proximal and distal ends provide equal or substantial equal resistance to expansion or that the proximal end provides greater resistance to expansion than the distal end.

Figure 14:
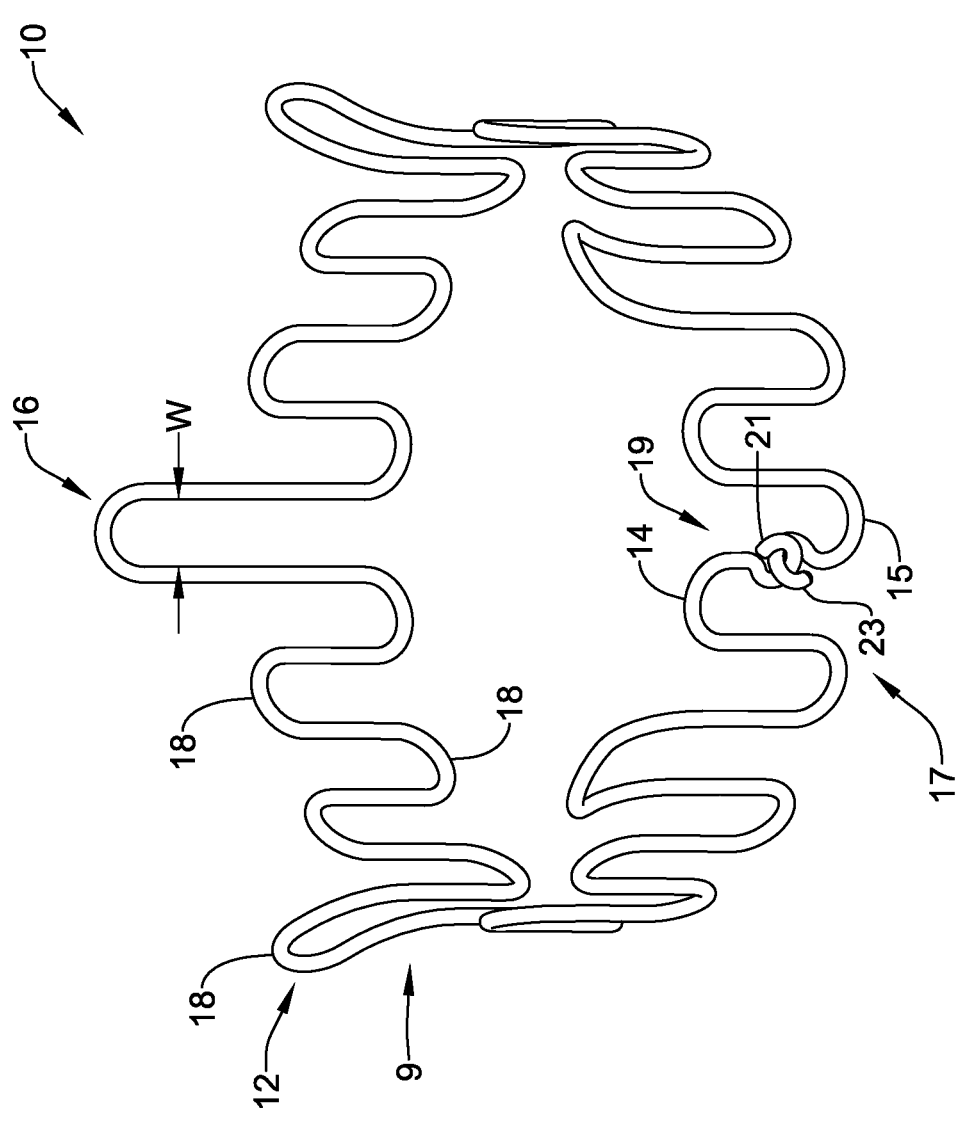
FIG. 14 depicts a schematic perspective view of an illustrative implantable device.

FIG. 14 illustrates an implantable device 10 which may be similar to the implantable device 10 depicted in FIG. 11, but with the wave pattern 12 having less frequent loops 18 on the first side 16 and more frequent loops 18 on the second side 17 of the implantable device 10. The spacing or width between each adjacent loop 18 may facilitate setting spring constants at the first side 16 and/or the second side 17 of the implantable device 10. The wave pattern 12 depicted in FIG. 14 may include a flared region 9 in the less frequent loops 18 on the first side 16. In contrast, the second side 17 of the wave pattern 12 may not include a flared region 9. Forming a wave pattern 12 that does not include a flared region 9 on the second side 17 may provide a greater contact area with the body tissue, which may create a more rigid implantable device 10, minimize or limit erosion of the body tissue at contact locations between the implantable device 10 and the body tissue, promote an increased growth of scar tissue adjacent the implantable device 10 relative to adjacent the first side 16 of the implantable device 10, and/or provide one or more other suitable benefits.

FIGS. 15 and 16 illustrate an implantable device 10 which may be similar to the implantable device depicted in FIG. 14, with a wave pattern 12 having less frequent loops 18 on the first side 16, and more frequent loops 18 on the second side 17 of the implantable device 10. The loops 18, depicted in FIGS. 15 and 16 on the first side 16 of the implantable device 10 may include a first width W1 and a second width W2, in which the first width W1 and the second width W2 may differ. The flared region 9 of the implantable device 10, as shown in FIGS. 15 and 16, may be formed at the point in which the loops 18 have the second width W2. In some cases, the second width W2 may be configured to create a flex pivot point based on narrowing of the wire geometry, but this is not required. The flared region 9 of the loops 18 may flare such that a contact location is provided between the implantable device 10 and the body tissue. The contact location may promote an increased growth of scar tissue adjacent the implantable device 10, and/or provide one or more other suitable benefits.

FIGS. 17 and 18 illustrate an implantable device 10 which may be similar to the implantable device depicted in FIG. 11, with a wave pattern 12 having loops 18 with differing heights. For example, as shown for example in FIG. 18, the loops 18 may include a first height H1, which may be larger relative to the loops 18 which may include a second height H2. The differing heights H1 and H2 of the loops 18 may provide differing contact locations along the wire structure 11 between the implantable device 10 and the body tissue to promote scar tissue growth in the configuration of the wire structure 11. Further the differing heights of the loops 18 may be utilized to configure the spring constant(s) of the implantable device 10 at particular locations along the implantable device 10.

FIG. 19 illustrates an implantable device 10 having a wave pattern 12 that does not have a flared region 9, but includes a wave pattern 12 having loops of differing heights. For example, FIG. 19 shows the implantable device 10 having a wave pattern 12 with substantially the same diameter at the first side 16 of the wave pattern 22 as at the second side 17 of the wave pattern 12. Forming a wave pattern 12 that does not include a flared region 9 may provide a greater contact area with the body tissue, which may create a more rigid implantable device 10, minimize erosion of the body tissue at contact locations between the implantable device 10 and the body tissue, promote an increased growth of scar tissue adjacent the implantable device 10, and/or provide one or more other suitable benefits. Further, due to the loops 18 having differing heights, the loops 18 adjacent the first side 16 of the implantable device 10 are spaced farther apart than the loops 18 adjacent the second side 17 of the implantable device 10, which may result in the first side 16 of the implantable device 10 having a spring constant that requires less force to overcome than the force needed to overcome a spring constant of the implantable device 10 adjacent the second side 17.

FIG. 20 illustrates a wave pattern 62 formed by a wire structure 61 that may be used for a wire structure of an implantable device, such as an implantable device 60 (e.g., the implantable device 60 may be similar to the implantable device 10, but this is not required). The wave pattern 62 may be configured to cause different portions of the wave pattern 62 to have different spring constants. The different spring constants resulting from the wave pattern 62 depicted in FIG. 20 may be based, at least in part, on a height, width, and/or otherwise spacing of loops 68 of the wave pattern 62. As shown in FIG. 20, the loops 68 may have a height dimension of one of height H1', height H2', height H3', or other suitable height, and the loops 68 may have a width dimension of one of a width W1', a width W2' or other suitable width, where the combined height and width dimensions of a loop 68 and of adjacent loops 68 may determine a spring constant of the wire structure 61 at or around the loop 68, similar to as discussed above. Further, as opposed to the wave patterns 42, 72 that are depicted as repeating over a length of the wire structures 41, 71 in FIGS. 21 and 22, the wave pattern 62 may not repeat over a length of the wire structure 61, as shown in FIG. 20, but this is not required. In some cases, the lack of a repeating pattern may be due to a desire to have a particular spring constant or rigidity of the wire structure 61 and/or a desired tissue growth pattern at a particular location along a circumference of the implantable device 60. Other rationales for such a configuration are contemplated.

FIG. 21 illustrates a wave pattern 42 formed by a wire structure 41 that may be used for a wire structure of an implantable device, such as an implantable device 40 (e.g., which may be similar to the implantable device 10, but this is not required). The wave pattern 42 may be configured to cause a first side 46 of the wire structure 41 to have a first spring constant and a second side 47 of the wire structure 41 to have a second spring constant, where the first spring constant is different than the second spring constant. The first and second spring constants, as depicted in FIG. 21, may be based, at least in part, on a height and/or a width of loops 48 of the wave pattern 42. As shown in FIG. 21, some loops 48 may have dimensions of a first height H1" and a first width W1", some loops 48 may have dimensions of a second height H2" and a second width W2", where the loops 48 with different dimensions may affect a local spring constant of the wire structure 41 and/or a local tissue grown around the wire structure 41.

FIG. 22 illustrates a wave pattern 72 formed by a wire structure 71 that may be used for a wire structure of an implantable device, such as an implantable device 70 (e.g., which may be similar to the implantable device 10, but this is not required). The wave pattern 72 may be configured to cause a first side 76 of the wire structure 71 and a second side 77 of the wire structure 71 to have a same or similar spring constant. The spring constant, as depicted in FIG. 22, may be based, at least in part, on a height H' and/or a width W' of loops 78 of the wave pattern 72.

FIGS. 23-25 illustrate configurations of wave patterns formed by wire structures that may be used in the implantable device (e.g., implantable devices 50, 80, 90, discussed below, which may all be similar to the implantable device 10 unless expressly indicated otherwise), where the wire structures include a coating or covering over at least a portion of the wire structure. When a coating or covering is utilized, one or more layers of materials may be positioned on and/or adjacent to the first side and/or the second side of the wave pattern. In some instances, the coating or covering may include an elastomeric or a non-elastomeric material, a biostable material, a drug eluting material, a material promoting growth of tissue, a material preventing growth of material, a bioabsorbale material, a biodegradable material, and/or other suitable material. For example, the coating or covering may be a polymeric material, such as silicone, silicone mesh, polytetrafluoroethylene, polyurethane, or the like, or other materials including, but not limited to, those disclosed herein. Further, the coating or covering may be or may include a drug coating designed to promote the growth of scar tissue. The coating(s) applied to the wire structures of the implantable devices 10 may be configured to affect or effect (e.g., by selection of material type, material location, material properties, etc.) a spring constant or rigidity of the implantable devices 10. Particular patterns of coatings may be applied to the wire structures to exact a desired spring constant, rigidity, and/or scarring/tissue growth at particular locations with respect to the implantable devices. The coatings applied to the wire structures depicted in FIGS. 23-25 are depicted as being clear such that the underlying wire structure is visible, but the coatings may not be clear and/or the underlying wire structure may not be visible through the coatings.

FIG. 23 depicts an implantable device 80, which may be similar to the implantable device 10, having a wave pattern 82 that may include a coating 88 on a second side 87 of the wire structure 81, while a first side 86 of the wire structure 81 may be free from a coating. In a further example, FIG. 24 depicts an implantable device 90, which may be similar to the implantable device 10, having a wave pattern 92 that may include a coating 98 on a first side 96 of the wire structure 91, where a second side 97 of the wire structure 91 may not be coated. The coating(s) applied to the wire structures 81, 91 may be configured to affect or effect (e.g., by selection of material type, material location, material properties, etc.) a spring constant or rigidity of the respective implantable devices 80, 90 and/or to promote tissue grown, and particular patterns of coatings may be applied to the wire structures 81, 91, as depicted in FIGS. 23 and 24 to exact a desired spring constant, rigidity, and/or scarring/tissue growth at sides 86, 87, 96, 97 of the implantable devices 80, 90.

FIG. 25 depicts a coating 58 which may encapsulate an entirety of a wire structure 51 utilized in an implantable device 50 (e.g., an implantable device similar to the implantable device 10) and may take a general form or shape or design of a wave pattern of the wire structure 51. In some instances, the wire structure 51 may include one or more layers (e.g., coverings, coatings, etc.) of material positioned on and/or adjacent to the first side 56 and/or the second side 57 of the wave pattern 52. Further, the coating 58 applied to wire structure 51 may be configured to affect a spring constant or rigidity of the implantable device 50 and/or tissue growth promotion. In one example, a thickness of the coating 58, a material type of the coating applied to the wire structure 51, and/or other material properties of the coating 58 may be selected such that the implantable device 50 has a desired spring constant when the coating is applied to the wire structure 51 and/or promotes scarring/tissue growth at one or more desired locations.

FIG. 26 depicts a coating 58 which may encapsulate an entirety of the wire structure 51 utilized in the implantable device 50 and may take a general ribbon and/or band form that may fill gaps between windings of the wave pattern of the wire structure 51. Although the portion of the implantable device 50 depicted in FIG. 26 is depicted in rectangular/linear form, the implantable device 50 may have an annular shape for placement around body tissue defining a lumen. The coating 58 may include one or more layers (e.g., coverings, coatings, etc.) of material positioned on the wire structure 51 to form the implantable device 50. In some cases, the coating 58 may be configured to affect a spring constant or rigidity of the implantable device 50 and/or tissue growth promotion. In one example, and similar to as discussed above with respect to the configuration of the implantable device 50 depicted in FIG. 25, a thickness of the coating 58, a material type of the coating 58 applied to the wire structure 51, and/or other material properties of the coating 58 may be selected such that the implantable device 50 has a desired spring constant when the coating is applied to the wire structure 51.

Further, although the coating 58 is depicted in FIG. 26 as extending beyond peaks (e.g., the wire structure 51 adjacent the first side 56) and valleys (e.g., the wire structure 51 adjacent the second side 57) of or in a wave pattern of the wire structure 51, the coating 58 may extend beyond the peaks in the wave pattern and not the valleys in the wave pattern, the coating 58 may extend beyond valleys in the wave pattern and not the peaks in the wave pattern, the coating 58 may extend beyond both the valleys and the peaks in the wave pattern (as depicted in FIG. 26), the coating 58 may extend beyond neither the valleys nor the peaks in the wave pattern, and/or the coating 58 may take on one or more other suitable configurations. In some cases, the shape of the coating 58 taking on a band or ribbon form as depicted in FIG. 26 may have a consistent configuration along a circumference of the implantable device 50 or may have different and/or inconsistent configurations along the circumference of the implantable device 50.

The coating 58 having a band or ribbon form may be formed using any suitable manufacturing technique. Example manufacturing techniques include, but are not limited to, forming techniques including molding techniques, additive techniques (e.g., three-dimensional printing, etc.), laminating techniques, subtraction techniques (e.g., etching, lathing, etc.), stretching techniques, and/or other suitable manufacturing techniques.

FIG. 27 depicts a schematic cross-section view of the implantable device 50 depicted in FIG. 26, taken along line 27-27 in FIG. 26. As shown in FIG. 27, the wire structure 51 may be encapsulated in the coating 58. Although the coating 58 is depicted in FIG. 27 as having thickness T' that is greater than the thickness T of the wire structure 51, the thickness T' of the coating 58 may be less than, equal to, or greater than the thickness T of the wire structure 51, as desired. Example values of the thickness T' of the coating 58 may include values of or between about 0.0005" to about 0.1875" and/or other suitable values.

FIG. 28 depicts an implantable device 10. The implantable device 10 may be formed from a material 20 using a molding technique and/or other suitable forming technique. When the implantable device 10 is formed from the material 20, the wire structure 11 may be omitted, but this is not required. The material 20 may be a polymeric material, such as silicone, silicone mesh, polytetrafluoroethylene, polyurethane, or the like, or other suitable materials including, but not limited to, those disclosed herein. The material 20 may be configured (e.g., a height, width, thickness, material type, shape, and/or other suitable properties may be selected to configure the material) to affect a spring constant or rigidity of the implantable device 10 depicted in FIG. 28. Further, the material 20 may be or may include a drug coating designed to promote the growth of scar tissue. In some cases, although not shown, the implantable device 10 depicted in FIG. 28 that includes the material 20 may encapsulate an entirety of a wire structure of an implantable device (e.g., the wire structure 11 of the implantable device 10), when a wire structure is included in the implantable device 10.

The materials that can be used for the various components of implantable device 10 (and/or other devices disclosed herein). For simplicity purposes, the following discussion makes reference to implantable device 10. However, this is not intended to limit the devices and methods described herein.

Implantable device 10 (and/or other devices disclosed herein) and/or other components of implantable device 10 (and/or other devices disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of implantable device 10 (and/or other devices disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of implantable device 10 (and/or other devices disclosed herein) in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of implantable device 10 (and/or other devices disclosed herein) to achieve the same result.

In some embodiments, a degree of Magnetic Resonance Imaging (MRI) compatibility is imparted into implantable device 10 (and/or other devices disclosed herein). For example, implantable device 10 (and/or other devices disclosed herein), or portions thereof, may be made of a material that does not substantially distort the image and create substantial artifacts (e.g., gaps in the image). Certain ferromagnetic materials, for example, may not be suitable because they may create artifacts in an MRI image. Implantable device 10 (and/or other devices disclosed herein), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of implanting a device around a body tissue structure, the method comprising:
  introducing an implantable device to a patient, the implantable device comprising:
    an elastic structure having a wave pattern;
  positioning the implantable device around the body tissue structure, and
  wherein a spring constant of the elastic structure changes along a longitudinal direction of the structure when the implantable device is positioned around the body tissue structure, and
  wherein the body tissue structure is at or adjacent a lower esophageal sphincter.

2. The method of claim 1, further comprising:
  straightening the elastic structure from the wave pattern into a linear structure.

3. The method of claim 2, wherein straightening the elastic structure comprises:
  gripping the elastic structure; and
  applying a pulling force to the elastic structure while gripping the elastic structure.

4. The method of claim 2, further comprising:
  repositioning the elastic structure around the body tissue structure, wherein the straightening of the elastic structure facilitates repositioning the elastic structure.

5. The method of claim 2, further comprising:
  removing the elastic structure from around the body tissue structure, wherein the straightening of the elastic structure facilitates removing the elastic structure.

6. The method of claim 1, wherein a first side of the wave pattern forms a flared region.

7. The method of claim 1, wherein the implantable device is configured to move radially inward and outward with the body tissue structure.

8. The method of claim 1, wherein the wave pattern is configured to allow passage of food from an esophagus of the patient to a stomach of the patient and limit reflux of contents from the stomach into the esophagus.

9. The method of claim 1, wherein the elastic structure includes a first side having a first spring constant and a second side having a second spring constant different than the first spring constant.

10. The implantable device of claim 9, wherein the first spring constant of the first side is greater than the second spring constant of the second side.

11. The implantable device of claim 1, wherein the elastic structure is at least partially formed from a bioabsorbable or biodegradable material and is configured to promote scar tissue at one or more locations at which the elastic structure is configured to contact the body tissue structure.

12. An implantable device for implantation around a body tissue structure comprising:
  an elastic structure having a wave pattern,

wherein the elastic structure is elastic so as to provide a pressure around the body tissue structure such that the pressure may change with movement of the body tissue structure, and
  wherein a spring constant of the elastic structure changes along a longitudinal direction of the elastic structure, and
  wherein the elastic structure is configured to straighten into a linear wire structure in response to a pulling force applied thereto.

13. The implantable device of claim 12, wherein the spring constant of the elastic structure is based on a configuration of the wave pattern.

14. An implantable device for implantation around a body tissue structure comprising:
  a structure configured to have an annular configuration and a linear configuration, and
  wherein the structure is elastic and configured to adjust radially outward in response to radially outward movement of the body tissue structure, and
  wherein a spring constant of the structure changes along a longitudinal direction of the structure when the structure is in the annular configuration, and
  wherein the structure is at least partially formed from a bioabsorbable or biodegradable material and is configured to promote scar tissue at one or more locations at which the structure is configured to contact the body tissue structure.

15. The implantable device of claim 14, wherein the structure includes a wire structure.

16. A method of implanting a device around a body tissue structure, the method comprising:
  introducing an implantable device to a patient, the implantable device comprising:
    an elastic structure having a wave pattern;
  positioning the implantable device around the body tissue structure; and
  straightening the elastic structure from the wave pattern into a linear structure, wherein straightening the elastic structure comprises:
    gripping the elastic structure; and
    applying a pulling force to the elastic structure while gripping the elastic structure, and
  wherein a spring constant of the elastic structure changes along a longitudinal direction of the structure when the implantable device is positioned around the body tissue structure.

17. A method of implanting a device around a body tissue structure, the method comprising:
  introducing an implantable device to a patient, the implantable device comprising:
    an elastic structure having a wave pattern;
  positioning the implantable device around the body tissue structure;
    straightening the elastic structure from the wave pattern into a linear structure; and
  repositioning the elastic structure around the body tissue structure, wherein the straightening of the elastic structure facilitates repositioning the elastic structure;
  wherein a spring constant of the elastic structure changes along a longitudinal direction of the structure when the implantable device is positioned around the body tissue structure.

18. A method of implanting a device around a body tissue structure, the method comprising:
  introducing an implantable device to a patient, the implantable device comprising:

an elastic structure having a wave pattern;

positioning the implantable device around the body tissue structure; and straightening the elastic structure from the wave pattern into a linear structure;

removing the elastic structure from around the body tissue structure, wherein the straightening of the elastic structure facilitates removing the elastic structure, and wherein a spring constant of the elastic structure changes along a longitudinal direction of the structure when the implantable device is positioned around the body tissue structure.

19. A method of implanting a device around a body tissue structure, the method comprising:

introducing an implantable device to a patient, the implantable device comprising:

an elastic structure having a wave pattern;

positioning the implantable device around the body tissue structure, and wherein a spring constant of the elastic structure changes along a longitudinal direction of the structure when the implantable device is positioned around the body tissue structure, and wherein the body tissue structure is at or adjacent an anal sphincter.

20. The method of claim 1, wherein the wave pattern is configured to permit passage of waste from a rectum of the patient at a desired time and mitigate inadvertent passing of waste from the rectum.

21. A method of implanting a device around a body tissue structure, the method comprising:

introducing an implantable device to a patient, the implantable device comprising:

an elastic structure having a wave pattern;

positioning the implantable device around the body tissue structure, and wherein a spring constant of the elastic structure changes along a longitudinal direction of the structure when the implantable device is positioned around the body tissue structure, and wherein the elastic structure includes a first side having a first spring constant and a second side having a second spring constant different than the first spring constant.

22. A method of implanting a device around a body tissue structure, the method comprising:

introducing an implantable device to a patient, the implantable device comprising:

an elastic structure having a wave pattern;

positioning the implantable device around the body tissue structure, and wherein a spring constant of the elastic structure changes along a longitudinal direction of the structure when the implantable device is positioned around the body tissue structure, and wherein the elastic structure is at least partially formed from a bioabsorbable or biodegradable material and is configured to promote scar tissue at one or more locations at which the elastic structure is configured to contact the body tissue structure.

* * * * *